United States Patent [19]

Wolff et al.

[11] Patent Number: 5,965,434

[45] Date of Patent: *Oct. 12, 1999

[54] AMPHIPATHIC PH SENSITIVE COMPOUNDS AND DELIVERY SYSTEMS FOR DELIVERING BIOLOGICALLY ACTIVE COMPOUNDS

[76] Inventors: Jon A. Wolff, 1122 University Bay Dr.; Vladimir Budker, 204 N. Segoe Rd. #513, both of Madison, Wis. 53705; Vladimir Gurevich, 2113 E. Johnson St., Madison, Wis. 53704

[ * ] Notice: This patent is subject to a terminal disclaimer.

[21] Appl. No.: 08/365,841

[22] Filed: Dec. 29, 1994

[51] Int. Cl.$^6$ .................................................... C12N 15/63
[52] U.S. Cl. .................... 435/320.1; 264/4.1; 264/4.3; 264/4.6; 424/490; 424/450; 428/402.2; 435/455; 435/458; 536/23.1; 514/44
[58] Field of Search ................... 428/402.2; 424/450, 424/490; 264/4.1, 4.3, 4.6; 514/44; 536/23.1; 435/320.1, 455, 458

[56] References Cited

U.S. PATENT DOCUMENTS 5,550,289   8/1996   Eppstein et al. ........................ 564/293

OTHER PUBLICATIONS

Kunitake et al., J. Am. Chem. Soc., 106, 1978–1983, 1984.
Boutorine et al., Biochimie, 76, 23–32, 1994.
Felgner, PL et al. Lipofection: A highly efficient, lipid-mediated DNA-transfection procedure. Proceedings of the National Academy of Sciences 84:7413–7417, Nov. 1987.

Solodin, I et al. A novel series of amphiphilic imidazolinium compounds for in vitro and in vivo gene delivery. Biochemistry 34:13537–13544, 1995.

Gao, X et al. A novel cationic liposome reagent for efficient transfection of mammalian cells. Biochem. Biophys. Res. Comm. 179:280–285, 1991.

Behr, J–P et al. Efficient gene transfer into mammalian primary pituitary endocrine cells with lipopolyamine–coated DNA. Proceedings of the National Academy of Sciences, 86:6982–6986, 1989.

Ledley, Ham. Gene. Ther., 6:1129–1144 (1995).

Coghlan, New Scientist, vol. 148:14–15 (1995).

*Primary Examiner*—Bruce R. Campell
*Assistant Examiner*—Dave Trong Nguyen
*Attorney, Agent, or Firm*—Rockey, Milnamow & Katz, Ltd.

[57] ABSTRACT

The present invention provides amphipathic lipid compounds comprising a hydrophilic, catonic, pH-sensitive moiety, the positive charge of which moiety increases as pH decreases over the pH range of 8.0 to 4.5. Vesicular delivery systems comprising such amphipathic compounds and the use of those systems for delivering biologically active substances to cells are also provided.

14 Claims, No Drawings

AMPHIPATHIC PH SENSITIVE COMPOUNDS AND DELIVERY SYSTEMS FOR DELIVERING BIOLOGICALLY ACTIVE COMPOUNDS

TECHNICAL FIELD OF THE INVENTION

This invention relates to amphipathic lipid compounds comprising a cationic, pH-sensitive, hydrophilic moiety, the positive charge of which moiety increases with decreasing pH over the range of 8.0 to 4.5, and vesicular delivery systems containing such compounds. This invention also relates to the use of pH-sensitive, cationic delivery systems for the delivery of biologically active compounds to cells in vitro and in vivo.

BACKGROUND OF THE INVENTION

The efficient delivery of biologically active compounds to the intracellular space of cells has been accomplished by the use of a wide variety of vesicles. One particular type of vesicle, liposomes, is one of the most developed types of vesicles for drug delivery. Liposomes are microscopic vesicles that comprise amphipathic molecules that contain both hydrophobic and hydrophilic regions. Liposomes can contain an aqueous volume that is entirely enclosed by a membrane composed of amphipathic molecules (usually phospholipids).

Liposome drug carriers have been under development since the 1970's. Liposomes are formed from one to several different amphipathic molecules. Several methods have also been developed to complex biologically active compounds with liposomes. A biologically active compound can be entrapped within the internal aqueous phase, within the lipid phase, or complexed to the outside of the liposome.

Liposomes can be divided into three groups based upon their overall size and lamellar structure. Small uni-lamellar vesicles (SUV), which are typically prepared by sonication, are 20 to 30 nm in diameter and contain one single lipid bilayer surrounding the aqueous compartment. Multi-lamellar vesicles (MLV) are prepared by simply mixing amphipathic molecules in an aqueous phase and contain multiple aqueous compartments and bilayers. Large uni-lamellar vesicles (LUV) are most commonly prepared by reverse-phase evaporation. After subsequent pore filtration, LUV's are usually 150 to 200 nm in diameter.

Liposomes can also be classified according to mechanisms by which they attach to a target cell. Gangliosides, polysacharrides and polymers such as polyethylene glycol have been attached to liposomes (termed "Stealth Liposomes") to decrease their non-specific uptake by the reticuloendothelial system in vivo. Antibodies, polysaccharides, sugars, and other ligands have been attached to liposomes to enable the tissue and cell specific delivery of biologically active compounds. Other cellular and viral proteins have also been incorporated into liposomes for targeting purposes and for their fusogenic properties.

Liposomes typically deliver a biologically active compound found within their aqueous space to target cells by fusing with either the plasma membrane or an internal membrane of the cell after endocytosis of the liposome. Fusion of the liposome membrane with the cellular membrane is one of the critical steps in the efficient delivery of substances to the cell. Certain types of liposomes are endocytosed by certain types of cells.

If a liposome is endocytosed by a receptor-mediated pathway, then it enters an endosome. In order for the biologically active compound contained within or associated with the liposome to reach its target sites and receptors, it is essential that the compound escape or be released from the endosome and avoid degradation in the lysosomes.

Knowledge of the phases in which liposomes exist has been used to design liposomes that are more efficient in delivering their contents to cells and fusing with the cellular membranes. Liposomes can exist in a variety of phases. The phases are classified by their lattice type, chain order, and curvature such as: a) micellar, two-dimensional hexagonal (HI), b) inverted micellar (HIII), c) two-dimensional oblique (P), d) one dimensional lamellar, bilayer (Lα), e), three-dimensional cubic (Q), and f) three-dimensional crystalline (C). The hydrocarbon chain order is characterized as: a) α, disordered or fluid, b) β-untilted ordered or gel, and c) β', tilted gel. In terms of the curvature, flat bilayer phases have zero curvature. Non-lamellar phases have non-zero curvaturess, type I (normal) phases have positive curvatures in which the interface curves towards the hydrocarbon chains and type II (inverted) phases have negative curvatures in which the interface curves away the hydrocarbon chains. Transitions between the phases can be induced by varying the phospholipid concentration (lyotropic), the temperature (thermotropic), and other conditions such as pH or ionic strength (isothermal).

On the basis of these principles of liposome phases, negatively-charged, pH-sensitive liposomes have been designed to release their contents outside the endosomes by taking advantage of the endosomes' acidification. In studies using specific ligands to carry pH probes into the endocytic pathway, the pH falls to pH 6.5 within 5 minutes of formation of the endocytic vesicles. Maximal acidification as low as pH 4.6 has been reported as the intravesicular pH in macrophages, but the pH may be higher in other cell types. In fibroblasts or epithelioid cells (CV-1), the endosome pH may be approximately 5.5. Several lipid-enveloped viruses such as influenza, vesicular stomatitis virus and Semliki Forest virus microinject their genome into the cytoplasm of the host cell by fusion of their surrounding endosome membrane after endosome acidification. Therefore, liposomes that will destabilize or fuse with the endosome membrane at mildly acidic pH can release their aqueous contents into the cytoplasm.

Liposomes of various compositions can be induced to fuse at a pH below neutral. The threshold can vary from pH 2 for phosphatidylserine-containing LUV's to near pH 7 for SUV's consisting of phosphatidylethanolamine (PE) and palmitoylhomocysteine. A series of PE bilayer stabilizers possessing titratable acidic headgroups have been utilized in the development of pH-sensitive liposomes. All of the negatively-charged, pH sensitive groups have been carboxylic acids as for example palmitoylhomocysteine, oleic acid, palmitic acid, N-succinyldioleoyl-phosphatidylethanolamine, 2,3-seco-5α-cholestan-2,3-dioic acid, double chain glycerol-based amphiphiles such as Nα(N-oleoyl-2-aminopalmitoyl)histidine (uses the carboxylic acid group in the histidine for pH sensitivity) and N-(N-oleoyl-2-aminopalmitoyl)serine.

Different mechanisms may be operative in proton-induced membrane fusion in the above pH-sensitive, negatively-charged liposomes. These pH-sensitive, negatively-charged liposomes include mixtures of lipids containing a carboxylic acid group and PE (phosphatidylethanoloamine). At high pH, the carboxylic acid group is negatively charged and the increased size of the head group stabilizes the PE-containing liposomes. Liposomes containing only PE at physiologic pH of 4.5–8 are prone to the HII-phase. The PE-rich liposomes which contain second "stabilizing" amphipaths can be stable at pH>pK of the amphiphile. At pH<pK protonation of the amphipath results in an uncharged or reduced-charge species that is unable to stabilize the PE-rich bilayer. The liposomes leak their aqueous contents and form larger structures with the coalescence of membrane components. Many pH-sensitive, PE-rich liposomes have been shown to deliver a variety of membrane-impermeant compounds to various cell types. The mechanism by which cytoplasmic delivery occurs has not been definitely demonstrated. It is not clear whether pH-sensitive liposomes undergo acid-triggered fusion with the lumenal side of the endocytic vesicle membrane or whether the pH-dependent collapse of large numbers of PE-rich liposomes within endocytic vesicles exerts a general detergent-like effect that leads to gross defects in the endosome's membrane.

Negatively-charged, pH-sensitive liposomes have been used to deliver DNA in a functional and target-specific manner in vitro and in vivo. Therefore, further investigation of the delivery mechanism of pH-sensitive liposomes is required. Negatively-charged, pH-sensitive liposomes have also been used to deliver proteins. In addition, negatively-charge liposomes have serious difficulties that include low-transfection efficiency, low encapsulation of DNA, sonication-induced DNA degradation and the requirement to separate the DNA-liposome complexes from "ghost" vesicles.

Various cationic metal ions and polycations have been shown to induce the fusion of negatively-charged liposomes. Polycations such as mellitin, polymixin B, polylysine and synthetic polymers such as polyethylenimine and poly(allylamine) have been shown to induce fusion at neutral pH while polymeric polycations such as polyhistidine and cetylacetyl(imidazol-4-ylmethyl)polyethylenimine (CAIPEI) induce fusion of negatively-charged liposomes at acidic pH. It is generally believed that these polymeric polycations induce fusion of negatively-charged liposomes by increasing their aggregation and presumably inducing lipid phase separation like the divalent cations. The polymeric nature of the cations is an absolute requirement for fusion since the monomeric or oligomeric cations do not induce fusion. While these polycations have been useful for studying liposome fusion they have not been used to deliver biologic substances into cells whether in culture or in the whole organism. In addition the polycations cause hemolysis and/or hemagglutination.

A variety of viral proteins such as F protein of Sendai virus, the HA protein of influenza virus, and the G protein of the vesicular stomatitis virus and toxins such as diptheria toxin and tetanus have also been shown to induce fusion of liposomes at acidic pH. Also, a variety of synthetic peptides such as the GALA peptide and peptides derived from the influenza virus hemagglutinin have also been shown to induce fusion of liposomes at acidic pH. In addition, cellular proteins such as insulin and clathrin induce fusion of negatively-charged liposomes.

In order to circumvent the above difficulties, much more efficient polynucleotide transfer in vitro has been accomplished with the use of positively-charged liposomes that contain cationic lipids. The cationic lipid, N-[1-(2,3-dioleyloxy)propyl]-N,N,N-trimethylammonium chloride (DOTMA) was the first cationic lipid used for DNA transfections. DOTMA was combined with dioleoylphosphatidylcholine (DOPE) to form liposomes that spontaneously complexed with polynucleotides (DNA and RNA) and enabled relatively efficient transfections. These cationic liposomes are simply mixed with the polynucleotide and then applied to the cells in culture. Complete entrapment of the DNA or RNA molecules occurs because the positively-charged liposomes naturally complex with negatively-charged polynucleotides. DNA has been shown to induce fusion of cationic liposomes containing DOTMA/DOPE. The procedure with the cationic lipids is generally as or more efficient than the commonly-used procedure involving the co-precipitation of calcium phosphate and DNA.

DOTMA/DOPE liposomes have, however, substantial cytotoxicity, particularly in vivo. A variety of cationic lipids have been made in which a diacylglycerol or cholesterol hydrophobic moiety is linked to a cationic headgroup by metabolically degradable ester bond. These have included 1,2-Bis(oleoyloxy)-3-(4'-trimethylammonio)propane (DOTAP), 1,2-dioleoyl-3-(4'-trimethylammonio)butanoyl-sn-glycerol (DOTB), 1,2-dioleoyl-3-succinyl-sn-glycerol choline ester (DOSC) and cholesteryl (4'-trimethylammonio)butanoate (ChoTB). However, there is no evidence of reduced cytotoxicity in comparison of these ester bond-containing cationic lipids as compared to DOTMA. Stearylamine, a cationic lipid has been used in liposomes but it had great cytotoxicity and was not been reported to mediate DNA transfer. Another detergent, cetyl-trimethylammonium bromide (CTAB) when combined with DOPE was able to mediate DNA transfection, but it had significant cytotoxicity. A series of cationic, non-pH sensitive lipids that included DORI (1,2-dioleoyl-3-dimethyl-hydroxyethyl ammonium bromide), DORIE (1,2-dioleyloxypropyl-3-dimethyl-hydroxyethyl ammonium bromide), and DMRIE (1,2-dimyristyloxypropyl-3-dimethyl-hydroxyethyl ammonium bromide) have been reported and studied. Other non-pH-sensitive, cationic lipids include: O,O'-didodecyl-N-[p-(2-trimethylammonioethyloxy)benzoyl]-N,N,N-trimethylammonium chloride, Lipospermine, DC-Chol (3β[N-(N', N"-dimethylaminoethane)carbonyl]cholesterol), lipopoly(L-lysine), cationic multilamellar liposomes containing N-(α-trimethylammonioacetyl)-didodecyl-D-glutamate chloride (TMAG), TransfectACE™ (1:2.5 (w:w) ratio of DDAB which is dimethyl dioctadecylammonium bromide and DOPE) (GIBCO BRL) and lipofectAMINE™ (3:1 (w:w) ratio of DOSPA which is 2,3-dioleyloxy-N-[20({2,5-bis[(3-aminopropyl)amino]-1-oxypentyl}amino)ethyl]-N,N-dimethyl-2,3-bis(9-octadecenyloxy)-1-propanaminium trifluoroacetate and DOPE)(GIBCO BRL).

Lipofectamine mediates the transfection of cells more efficiently than lipofectin (DOPTMA/DOPE) formulations (considered the standard for comparison purposes), but it also has greater cytotoxicity.

All of the cationic lipids mediate transfection only when the cationic lipid/DNA complexes have a positive-to-negative charge ratio of at least one and a half. As a result, serum, which contains negatively-charged components, inhibits transfection to some extent with all the cationic lipid formulations (Lipofectin, LipofectAMINE, LipofectACE, and DOTAP). Chondroitin sulfate type B was a potent inhibitor of transfection with Lipofectin. LipofectAMINE, which is the most efficient cationic lipid transfection reagent, was inhibited the most by serum. Transfection is substantially inhibited if DNA and cationic lipids are mixed in the presence of serum. Cationic lipid liposomes also completely and stochiometrically inhibited the transfer of plasmid DNA into muscle in vivo. Histologic studies showed that the positively-charged DNA/cationic lipid complexes bound to the negatively-charged extracellular matrix and never gained access to the cellular membrane of the muscle cells.

BRIEF SUMMARY OF THE INVENTION

In one aspect, the present invention provides amphipathic compounds of formula I:

A—B—C  (I)

wherein

A is a hydrophobic moiety comprising a $C_6$–$C_{24}$ alkane, $C_6$–$C_{24}$ alkene, sterol, steroid, lipid, fatty acid or hydrophobic hormone;

B is a spacer moiety comprising an alkane, alkene, ester, ether, glycerol, amide, heteroatom or a molecule that is cleaved under physiological conditions; and C is a cationic, hydrophilic, pH-sensitive moiety comprising a primary, secondary or tertiary amine, an amine containing heterocycle, guanidine, hydrazine, a hydroxylamine or a thiuronium derivative.

In a preferred embodiment, the fatty acid is palmitic acid, oleic acid, stearic acid or myristic acid.

In one embodiment, an amphipathic compound containing a fatty acid has the formula II, below:

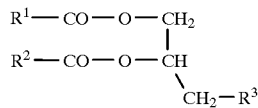

wherein $R^1$ and $R^2$ are independently $CH_3(CH_2)_{14}$, $CH_3(CH_2)_{12}$ or $CH_3(CH_2)_7CHCH(CH_2)_7$; and $R^3$ is 1-methylimidazole, imidazole, 4,9-dioxo-1,12-dodecanediamine, cysteamine, 1-(3-aminopropyl) imidazole, morpholine, 4-aminopyridine, pyridine, hydrazine, thiuronium or piperazine.

Preferred amphipathic compounds corresponding to formula II have the structure:

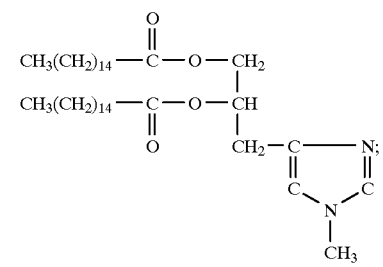

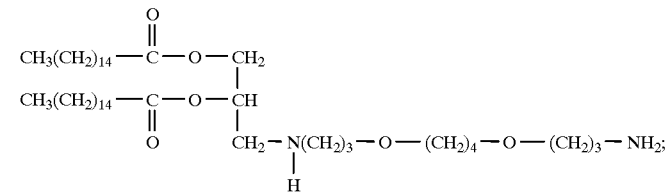

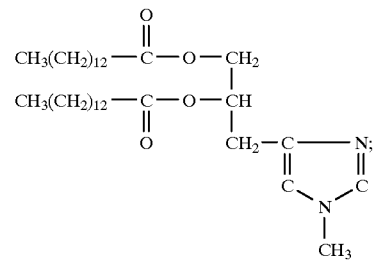

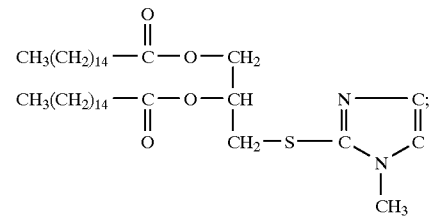

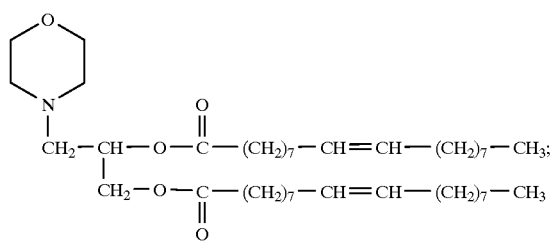
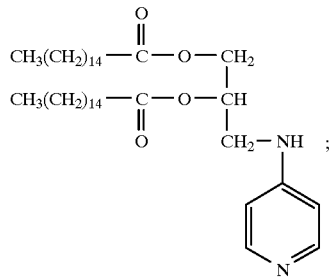
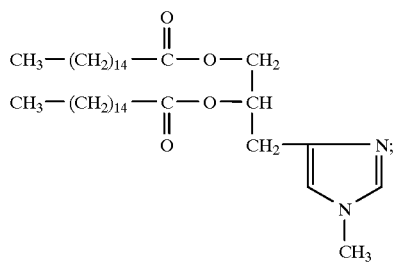
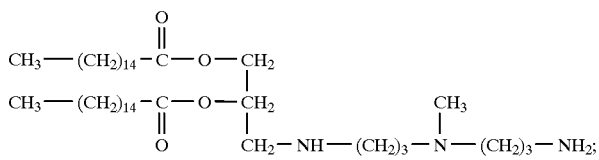
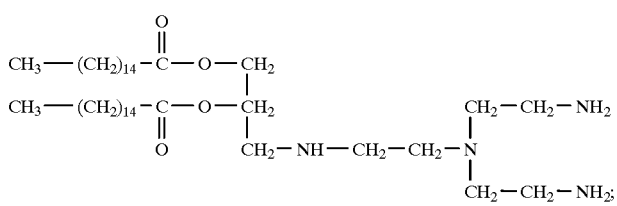
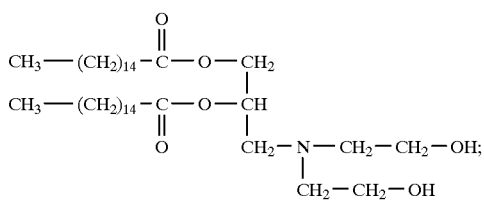
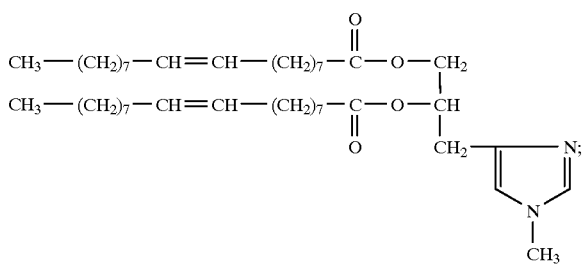

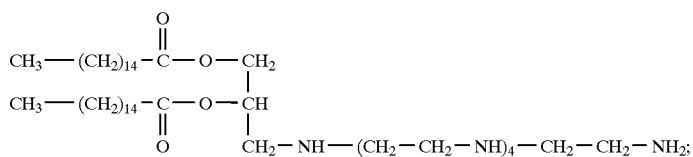

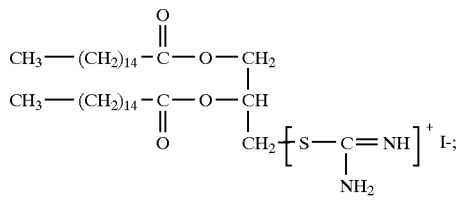

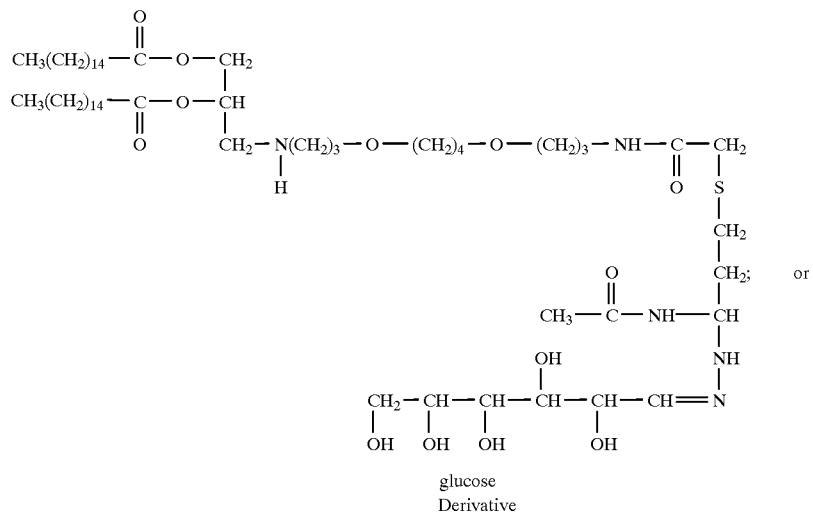

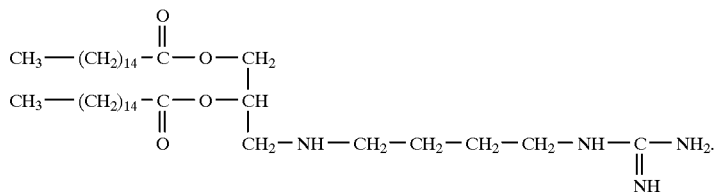

In another embodiment, an amphipathic compound containing a fatty acid has the formula III, below:

$$R^1-CO-O-CH_2$$
$$R^2-CO-O-C-R^3$$
$$R^4-CO-O-CH_2$$
(III)

wherein $R^1$, $R^2$ and $R^4$ are each independently $CH_3(CH_2)_{14}$, $CH_3(CH_2)_{12}$ or $CH_3(CH_2)_7CHCH(CH_2)_7$; and $R^3$ is Tris(2-aminoethyl)amine, 3,3'-diamino-N-methyldipropylamine hydroxylamine, diethanol amine, pentaethylenehexamine.

A preferred compound corresponding to formula III has the structure:

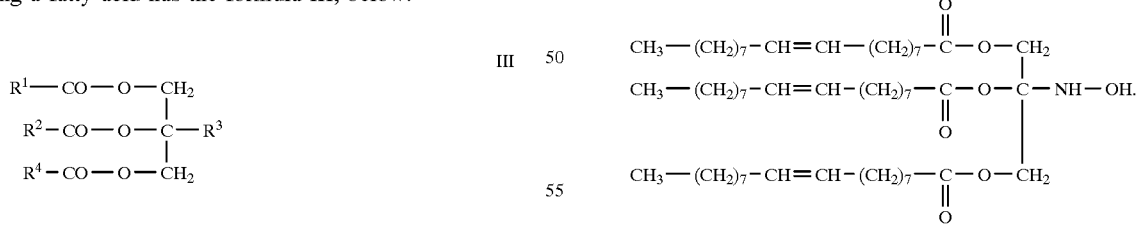

In yet another embodiment, an amphipathic compound containing a fatty acid has the structure:

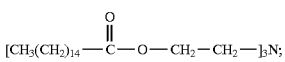

-continued

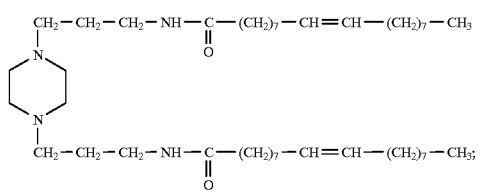

or

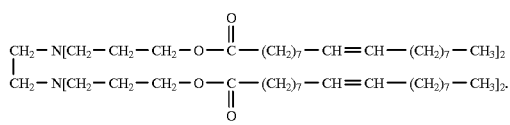

In yet another embodiment, an amphipathic compound comprises:

(a) at least one hydrophobic moiety, which is a steroid derivative;

(b) at least one spacer moiety comprising an alkane, alkene, ester, ether, glycerol, amide, heteroatom or a molecule that can be cleaved under physiological conditions; and (c) at least one cationic, hydrophilic, pH-sensitive moiety comprising a primary, secondary or tertiary amine, an amine containing heterocycle, guanidine, hydrazine, a hydroxylamine or a thiuronium derivative.

In a preferred embodiment, an amphipathic compound containing a steroid derivative has the structure:

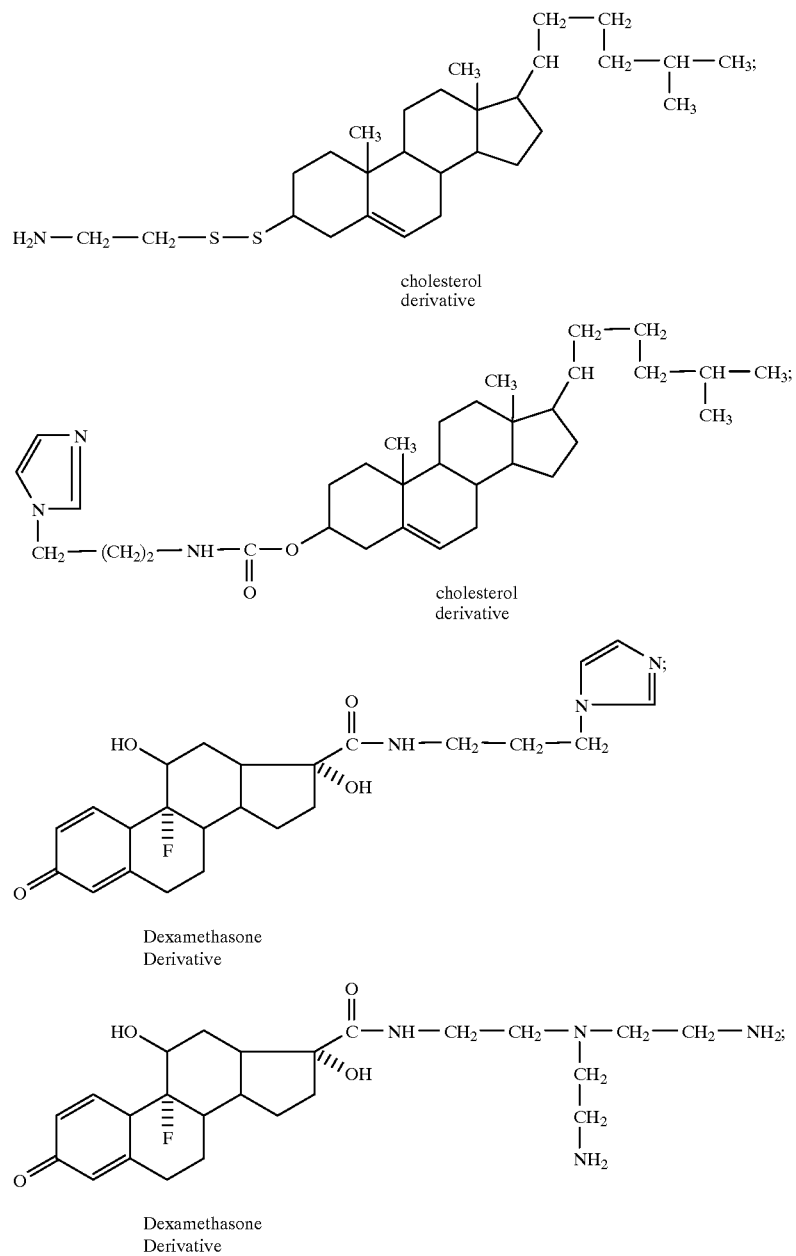

or

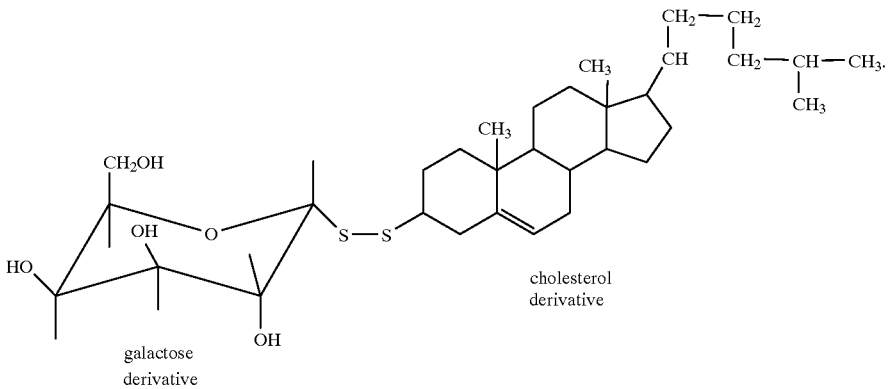

galactose
derivative cholesterol
derivative

In yet another aspect, the present invention provides a delivery system for biologically active substances comprising a plurality of vesicles, wherein each vesicle contains an amphipathic compound of formula I:

A—B—C  (I)

wherein
A is a hydrophobic moiety comprising a $C_6$–$C_{24}$ alkane, $C_6$–$C_{24}$ alkene, sterol, steroid, lipid, fatty acid or hydrophobic hormone;
B is a spacer moiety comprising an alkane, alkene, ester, ether, glycerol, amide, heteroatom or a molecule that is cleaved under physiological conditions; and
C is a cationic, hydrophilic, pH-sensitive moiety comprising a primary, secondary or tertiary amine, an amine containing heterocycle, guanidine, hydrazine, a hydroxylamine or a thiuronium derivative.

Preferably, a delivery system of the present invention comprises a target recognition group, which recognition group is preferably contained within the hydrophilic, cationic, pH-sensitive moiety.

In a preferred embodiment, vesicles are liposomes. In another embodiment, a delivery system of the present invention comprises a biologically active substance such as a polypeptide or a polynucleotide.

In yet another aspect, the present invention provides a process of delivering a biologically active substance to a cell comprising exposing the cell to the biologically active substance in the presence of a delivery system of the present invention. In a preferred embodiment, the biologically active substance is a polynucleotide such as a DNA molecule.

Where the cell is located in a living organism, the biologically active substance and the delivery system is administered to the organism. Preferably, the delivery system comprises liposomes that are complexed with the biologically active substance.

In still yet another aspect, the present invention provides a process of transfecting a cell with a polynucleotide comprising exposing the cell to the polynucleotide in the presence of the delivery system of the present invention. Where the cell being transfected is located in a living organism the polynucleotide and the delivery system are administered to the organism.

In still yet another aspect, the present invention provides a process of increasing the expression of an encoding polynucleotide in a cell comprising exposing the cell to the encoding polynucleotide in the presence of a the delivery system of the present invention.

The present invention provides amphipathic lipid compounds comprising a hydrophilic, cationic, pH-sensitive moiety, delivery systems comprising vesicles that contain such amphipathic compounds and methods of using such delivery systems for delivering biologically active substances to cells. An amphipathic compound of the present invention has particular utility in the design and preparation of cationic, pH-sensitive liposomes.

pH-sensitive, cationic liposomes have reduced positive charges at the appropriate pH and avoid becoming bound to the extracellular matrix and, thus, gain access to cellular membranes in vivo. These new pH-sensitive, cationic lipids combine the advantages of the previously developed, non-pH-sensitive cationic liposomes with those of anionic, pH-sensitive liposomes. At low pH, the liposomes assume a positive charge and spontaneously package DNA (or other polynucleotides such as RNA or oligonucleotides). The pH is then raised to reduce the charge of the liposomes to avoid the negative-charges of the extracellular matrix or blood.

The design of cationic, pH-sensitive liposomes is counter to considerations of pH-induced phase changes that underlie the design of pH-sensitive, negatively-charged liposomes where the induction of HII-formation by having the negative-charge of the carboxylic acid-containing lipids become reduced, which in turn reduces its hydrophilic head size, no longer stabilizes PE in the lamellar phase, and causes the transition to HII phase which is fusogenic. pH-sensitive, cationic lipids do the opposite. Their positive charge increases at low pH, which increases the hydrophilic head size and causes transition to HI phase.

Unexpectedly, pH-sensitive, cationic liposomes fuse at pH's at the low end of the physiologic range of 4.5 to 8. They can efficiently deliver a variety of compounds and biologically-active substances to cells. They can also deliver DNA much more efficiently than non-pH-sensitive, cationic lipids into cells and they can efficiently deliver DNA into muscle in vivo. In summary, the present invention combines the benefits of cationic-lipid and pH-sensitive liposomes (previously anionic) to produce novel formulations of liposomes that can deliver DNA and other substances into cells in culture and in the whole organism with greater efficiency and less toxicity than heretofore described.

DETAILED DESCRIPTION OF THE INVENTION

I. Amphipathic Lipid Compounds

The general structures and preferred structures of the amphipathic lipid compounds are described above in the Brief Summary of the Invention.

The hydrophobic moiety, A, can be an alkane, an alkene, a fatty acid or a steroid derivative. Preferably, the alkane and alkene comprise from about 6 to about 24 carbon atoms. In a like manner, a fatty acid preferably contains from 6 to 24 carbon atoms and, more preferably from about 12 to 20 carbon atoms. A fatty acid can be either saturated or unsaturated. In a preferred embodiment, the fatty acid is palmitic acid, oleic acid, stearic acid or myristic acid.

As used herein, the phrase "steroid derivative" means a sterol, a steroid, a steroid hormone, or an analog or derivative thereof. Preferred steroid derivatives are sterols, steroid hormones and analogs or derivatives thereof. Preferably, the sterol is cholesterol and the steroid hormone is dexamethasone.

An amphipathic compound of the present invention is prepared using standard synthetic procedures and commercially available starting materials as is well known in the art. A detailed description of the preparation of exemplary and preferred amphipathic compounds is set forth hereinafter in Example 1.

The hydrophobic moiety and the hydrophilic, cationic, pH-sensitive moiety are linked via a spacer group. The spacer group can be any linker known to those skilled in the art to enable one to join a hydrophobic moiety with the hydrophilic moiety. Preferred spacer groups include, but are not limited to $C_1$ to $C_{12}$ alkyl, $C_1$–$C_{12}$ alkenyl, ester, ether, glycerol, amide and heteroatoms. For example, the hydrophilic, cationic, pH-sensitive moiety can be linked to the same fatty acid though the use of a glycerol moiety, wherein the same fatty acids are linked to the glycerol moiety by an ester linkage. In another example, a cholesterol derivative is linked to a hydrophobic, cationic, pH-sensitive moiety through a heteroatom linkage, in particular a disulfide linkage or an amide linkage.

The hydrophobic moiety and hydrophilic, cationic, pH-sensitive moiety can also be linked via a spacer group or other linkage that is cleavable under physiological conditions (e.g., the intracellular environment). Exemplary such cleavable linkages are disulfide bridges or an enzyme-sensitive group.

III. Delivery Systems

In another aspect, the present invention provides a delivery system for delivering biologically active substances to cells. A delivery system of the present invention comprises a plurality of vesicles, each of which contains or incorporates an amphipathic compound or molecule. That amphipathic compound comprises:

(a) at least one hydrophobic moiety, each of which is selected from the group consisting of $C_6$–$C_{24}$ alkane, $C_6$–$C_{24}$ alkene, fatty acids, steroids, and steroid derivatives;

(b) at least one cationic, hydrophilic, pH-sensitive moiety comprising an amine, the positive charge of which pH-sensitive moiety increases with decreasing pH over the pH range of from about 8 to about 4.5; and (c) a spacer group linking the hydrophobic moiety and the cationic, pH-sensitive moiety, which spacer group is selected from the group consisting of $C_1$–$C_{12}$ alkane, $C_1$–$C_{12}$ alkene, ester, ether, glycerol, amide and heteroatoms.

Preferred amphipathic molecules used in a delivery system of the present invention are the same as set forth above.

A delivery system of the present invention is made using standard techniques well known to those of skill in the art. A detailed description of the preparation and use of preferred delivery systems of the present invention are set forth hereinafter in the Examples.

In a preferred embodiment, a delivery system of the present invention further comprises a target recognition group. A target recognition group is a chemical group that recognizes and becomes associated with (e.g., binds to) a target cell. In this way, a delivery system can be used to deliver a biologically active substance to a particular cell type. Exemplary target recognition groups are antibodies. A target recognition group can be attached to any component of an amphipathic compound using standard procedures well known to those skilled in the art. For example, a target recognition group can be a hydrophilic ligand such as a carbohydrate. Examples of carbohydrates include glucose as in compound 20 or galactose as in compound 18. Examples of hydrophobic target recognition groups include dexamethasone and cholesterol, such as in compounds 5, 5a, 6, 11, 12, 13 and 18.

Several advantages flow from the systems, compounds, and methods of the present invention. One of the advantages of the methods and materials disclosed herein is that they permit up to 100% entrapment of polyanionic substances by an exceedingly convenient and practical protocol. Another advantage of a delivery system of the present invention is that it is not subject to instability due to leakage of the entrapped polyanionic substance. Still another advantage is that the convenient and practical methodology disclosed herein yields compositions of matter with unique properties enabling entry of the entrapped polyanionic substance, such as DNA, into living cells. This property of the lipid/polyanion complex enables the expression of biologically activities to extents not previously seen in these cells. Further, this methodology leads to results in muscle in whole organisms that have not been obtained with conventional liposomes, pH-insensitive cationic (positively-charged) liposomes or pH-sensitive, anionic (negatively-charged) liposomes.

The pH-sensitive, positively-charged delivery systems, particularly liposomes, of this invention are pharmaceutically advantageous; these pH-sensitive, cationic materials enable the better uptake of pharmaceutical materials by the cells.

The uniqueness of such pH-sensitive, cationic delivery systems depends on the chemical structure of the amphipathic compounds that contain cationic groups whose positive charge increases with decreasing pH. Increasing the charge of these head groups within liposomes, increases the fusogenic properties of the liposomes. The increased charge of the head groups within the liposome changes the overall steric and ionic forces of the liposome lipid bilayer and favors the formation of HI phase which unpredictably enables efficient fusion with the cell. The decreasing pH can occur after the liposomes are endocytosed by cells and enter the acidic endosomes or in a novel embodiment, the pH-sensitive cationic liposome/polyanionic complexes are injected at a pH slightly above physiologic pH (e.g., 7.5 to 8.5) and exposure of the liposomes to the physiologic pH of 7.4 then induces fusion of the liposomes with the cells. Solutions containing the liposomes at pH greater than 7.4 can be tolerated by tissues without causing significant damage to the tissues. At pH's greater than 7.4, the pH-sensitive, cationic liposomes have a decreased positive charge and thereby avoid inactivation by negatively-charge extracellular matrix and gain better access to the cell membranes. In another novel embodiment, the pH-sensitive, cationic liposomes enable the intracellular delivery of DNA wherein the liposome/DNA complexes are formed in situ and in vivo.

The use of pH-sensitive, cationic liposomes for delivery of biologically-active substances including polyanions, polynucleotides, RNA, and DNA represents a major advance in liposome technology beyond the previously-described non-pH-sensitive, cationic liposomes and pH-sensitive, anionic liposomes. In a sense, the present invention combines the advantages of each of these previously-described liposome technologies. Unlike, pH-sensitive, anionic liposomes, the present delivery system comprising pH-sensitive, cationic liposomes, can encapsulate polyanionic substances with almost 100% efficiency, are not leaky or unstable in the presence of divalent actions such as $Ca^{+2}$ or $Mg^{+2}$, or serum or blood, and are much more efficient in delivering polyanions into cells. Unlike, non-pH-sensitive, cationic liposomes, the delivery systems of the present invention are more efficient in delivering polyanions into cells, have less cytotoxicity, enable the more efficient intracellular delivery of polyanions such as DNA into cells (e.g., muscle cells within the whole organism), can deliver intracellularly polyanionic substances when the net charge of the liposome/polyanion complex is neutral or negative, and can aid the delivery of intracellularly polyanionic substances wherein the said pH-sensitive, cationic lipids are injected separately from the polyanionic substance such as DNA.

IV. Methods of Use

A. A Process of Delivering a Biologically Active Substance to a Cell

In another aspect, the present invention provides a process of delivering a biologically active substance to a cell. In accordance with that process, a target cell (a cell to which the substance is to be delivered) is exposed to the biologically active substance in the presence of a delivery system of the present invention. Preferred such delivery systems are the same as set forth above. A target cell can be located in vitro (cell culture), in situ or in vivo (in a living organism).

As used herein, the phrase "biologically active substance" means any substance having the ability to alter the function of a living cell, tissue or organism. A biologically active substance can be a drug or other therapeutic agent. A biologically active substance can also be a chemical that interacts with and alters the function of a cell. By way of example, a biologically active substance can be a protein or peptide fragment thereof such as a receptor agonist or antagonist.

In addition, a biologically active substance can be a polynucleotide. As used herein, a polynucleotide is meant to include both DNA and RNA sequences of varying length. A DNA polynucleotide can be a gene, transgene, oligonucleotide, antisense sequence, cDNA sequence and the like. In a similar manner, a RNA polynucleotide can be a complete mRNA molecule, ribozyme or a short antisense sequence. Because of the cationic nature of a delivery system of the present invention, it is preferred that the biologically active substance have a net negative charge (polyanionic).

Where the target cell is located in vitro, the biologically active substance, and the delivery system are typically added to the culture medium in which the cell is being cultured. The active substance and delivery system can be added to the medium either simultaneously or sequentially. Alternatively, the biologically active substance and the delivery system can be formed into a complex and then added to the medium. A complex between a biologically active substance and a delivery system of the present invention can be made by contacting those materials under appropriate reaction conditions. Means for making such complexes are set forth hereinafter in the Examples.

Where the target cell is located in vivo, the biologically active substance and the delivery system are typically administered to the organism in such a way as to distribute those materials to the cell. The materials can be administered simultaneously or sequentially as set forth above. In one embodiment, the biologically active substance and the delivery system are administered as a complex. The delivery system and biologically active substance can be infused into the cardiovascular system (e.g., intravenously, intraarterially), injected directly into tissue containing the target cell (e.g., intramuscularly) or administered via other parenteral routes well known to one skilled in the art.

As set forth above, a delivery system can be prepared so as to contain a target recognition group, which group serves to direct the biologically active substance to particular cells with a high degree of efficiency.

Because of the cationic and pH-sensitive nature of a delivery system of the present invention, the use of such a system is particularly effective in vivo where there are differences in the pH of the extracellular and intracellular compartments. The advantages of using a cationic, pH-sensitive delivery system are shown hereinafter in the Examples.

B. Process of Transfecting a Cell with a Polynucleotide

Despite remarkable accomplishments in cloning genes relevant to many diseases and in developing a variety of new gene therapy methods in both animal and human models, there remains to be solved the challenging problem of efficiently transferring and stably expressing polynucleotides such as transgenes in appropriate tissues. Several new methods of gene transfer into postnatal somatic tissue are under development in many laboratories. They can be divided into two general approaches: those using direct transfer into cells in vivo and those using indirect methods involving the re-implantation of genetically-modified cells.

Indirect transplantation generally complicates a procedure in terms of risk, difficulty, efficacy, and cost. For example, bone marrow transplantation requires cytoablation, with accompanying mortality and morbidity. The transplantation of retrovirally infected hepatocytes requires a partial hepatectomy. Even if these experimental procedures eventually prove to be safe and effective, they may remain technically difficult to perform and costly, and therefore restricted in their availability. Direct gene therapy, on the other hand, is easier to perform and less risky, and therefore more widely applicable.

Direct gene therapy can be divided into two categories: those involving viral vectors and those involving plasmid DNA delivery. Direct viral methods include adenoviral vectors, herpes vectors, and retroviral infection of hepatectomized liver, endothelial cells or damaged muscle. Direct plasmid methods include polylysine conjugates, liposomes, cationic lipids, the biolistic "gun", and naked DNA.

It has been shown that skeletal and cardiac muscle have the unusual ability to take up and express naked plasmid DNA injected into their extracellular spaces in vivo. Plasmid DNA has been stably expressed for at least two years in muscle, which indicates that muscle is an attractive target tissue for the further development of direct plasmid DNA transfer technology. The injection of naked DNA into muscle has also been proposed as a very effective immunization approach and as a method to secrete proteins into the general circulation. However, efforts to develop this technique into a clinically-viable gene therapy has been stymied by the inability to express plasmid DNA in more than 1% of the myofibers in rodents and even less in monkeys. Given the ability for plasmid DNA to stably express in muscle indefinitely and the large number of applications that could use muscle as a "vehicle or platform" for foreign gene expression, any delivery system that can increase the plasmid transfection efficiency of muscle in vivo and in situ would have great pharmaceutical, medical, and veterinarian utility.

The relative merits of the two types of direct gene therapy, viral and plasmid, have yet to be determined. Transgenes within plasmids and viral vectors have been directly expressed in a variety of rodent tissues, including muscle, lung, brain and liver. Recently, adenoviral vectors have been shown to infect rodent muscle, lung and liver, but the efficiency and safety of adenoviral vectors in older mice and larger species, including primates, need to be proven.

Aside from efficiency, plasmid-based vectors appear to offer some advantages over viral vectors. Some viral vectors, such as herpes or adenoviral vectors, may retain viral genes and promoters that could express in human cells under certain conditions, causing immune or other adverse effects. Viral vectors are also difficult to scale up for human use, whereas plasmid DNA can be scaled-up in pilot plant 70-L culture vessels. Improvements in plasmid purification by column chromatography could further reduce the cost of plasmid preparation.

The currently-available cationic lipids (not pH-sensitive) can mediate gene transfer efficiently in vitro but relatively poorly in vivo. In fact, in muscle of the whole organism, the previously-developed cationic lipids actually inhibit the uptake of naked plasmid DNA. Cationic lipid-DNA complexes became bound to the negatively-charged extracellular matrix and never gained access to the cellular membrane. This observation suggests that any cationic lipid would be unable to mediate the transfection of DNA into muscle. Furthermore, blood contains several negatively-charged components such as heparin that inhibit transfection with cationic lipid/DNA complexes.

In another aspect, the present invention provides a process of transfecting a cell comprising exposing the cell to a polynucleotide in the presence of a delivery system of the present invention. The cell can be located in vitro, in situ or in vivo. Means for exposing the cell are the same as set forth above. Any cell can be transfected with a process of the present invention. Preferably, the cell is a muscle cell and, more preferably a cardiac or skeletal muscle cell. Details of transfecting muscle cells with a polynucleotide and a delivery system of the present invention are set forth hereinafter in the Examples.

Not only can a process of the present invention be used to transfect a cell but the transfection is shown to result in a marked increase in the expression of the transfected polynucleotide (See Examples, hereinafter). Thus, a delivery system of the present invention has use in a process of increasing polynucleotide expression in a cell.

The following Examples illustrate particular embodiments of the present invention and are not limiting of the claims and specification in any way.

EXAMPLE 1

Synthesis of Amphipathic Compounds

Thin Layer Chromatography (TLC) Systems

System [1]-dichloromethane/methanol 9:1
TLC plates-Kieselgel 60F254 from EM Science
System [2]-dichlormethane/methanol 8:2
TLC plates-Kieselgel 60F254 from EM Science
System [3]-dichloromethane/methanol 6:4
TLC plates-Kieselgel 60F254 from EM Science
System [4]-dichloromethane
TLC plates-Kieselgel 60F254 from EM Science
System [5]-heptane/ethylacetate 9:1
TLC plates-Baker-Flex cellulose
System [6]-ethanol
TLC plates-Baker-Flex cellulose
System [7]-Acetonitrile/diethanolamine 9:1
TLC plates-Baker-Flex cellulose
System [8]-45% methanol-45% tetrahydrofuran-10% acetic acid
TLC plates-Whatman MKC18 reverse phase Compound 1

A. Structure

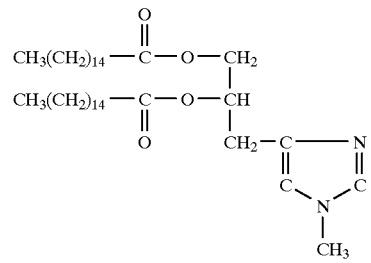

B. Synthesis 136 mg (0.2 mmol) of 1,2-dipalmitoyl-3-iodo-rac-3-deoxyglycerol was dissolved in 2 ml of dioxane and mixed with 24 µl (0.3 mmol) of 1-methylimidazole. The reaction mixture was then stirred for 16 hours at 70° C. Dioxane was evaporated and the residue was dissolved in chloroform and mixed with an equal volume of double-distilled water. After centrifugation and separation, the water layer was discarded. This extraction with water was repeated twice more. The chloroform layer was mixed with 3 volumes of acetonitrile and two thirds of the mixture volume was slowly evaporated under vacuum. Title Compound 1 was collected as a filtrate and dried under vacuum overnight. Yield was 128 mg (84% of the theoretical yield) of white crystals with:

Melting point 86°±1° C.

$R_f$=0.30 in the system [1]-dichloromethane/methanol ratio 9/1.

$R_f$=0.62 in the system [2]-dichloromethane/methanol ratio 8/2. TLC plates-Kieselgel $60F_{254}$ from EM-science.

IR: 2916, 2849 (alkane); 1240, 662 (methlyimidazole ring); 1740, 1172 (ester)

Compound 1 was also prepared as follows. 310 mg of 3-bromo-1,2-propanediol (2 mmol) in 3 ml of dioxane was mixed with 800 µl (10 mmol) of 1-methyl-imidazole. The reaction mixture was stirred for 16 hours at 70° C., mixed with 1,517 µl (5 mmol) of palmitoyl chloride and stirring was continued for another 24 hours at 70° C. The Title Compound 1 was purified as described above. Yield was 1326 mg (87% theoretical) of white crystal with melting point (uncorrected) of 86±1° C. Rf=0.30 in the system [1] (dichloromethane/methane mol ration 9/1). Rf=0.62 in the system [2]-dichloromethane/methane mol ratio of 8/2). TLC plates Kieselgel 60F254 from EM Science.

Compound 2

A. Structure $$CH_3(CH_2)_{14}-\overset{O}{\overset{\|}{C}}-O-CH_2$$
$$CH_3(CH_2)_{14}-\overset{\|}{\underset{O}{C}}-O-CH$$
$$CH_2-\underset{H}{N}(CH_2)_3-O-(CH_2)_4-O-(CH_2)_3-NH_2$$

B. Synthesis 136 mg (0.2 mmol) of 1,2-dipalmitoyl-3-iodo-rac-3-deoxyglycerol was dissolved in 2 ml of dioxane and mixed with 64 µl (0.3 mmol) of 4,9-dioxa-1,12-dodecanediamine. The reaction mixture was then stirred for 16 hours at 70° C. Dioxane was evaporated and the residue was dissolved in chloroform and mixed with an equal volume of double-distilled water. After centrifugation and separation, the water layer was discarded. This extraction with water was repeated until the water layer contained no significant amounts of amines as detected by ninhydrine reaction. The chloroform was then evaporated and the residue was re-crystallized from hot acetonitrile. Yield 134.4 mg (76% theoretical) of white crystals with:

Melting point 71°±1° C.

$R_f$=0.45 in the system [1]-dichloromethane/methanol ratio 9/1.

$R_f$=0.67 in the system [2]-dichloromethane/methanol ratio 8/2. TLC plates-Kieselgel 60F$_{254}$ from EM-science.

IR: 2919, 2851 (alkane); 1735, 1169 (ester); 1120 (ether); 3309, 840 (amine, primary); 3309, 1013 (amine, secondary)

Compound 3

A. Structure $$CH_3(CH_2)_{12}-\overset{O}{\overset{\|}{C}}-O-CH_2$$
$$CH_3(CH_2)_{12}-\overset{\|}{\underset{O}{C}}-O-CH$$
$$CH_2-C\underset{\underset{CH_3}{N}}{\overset{N}{\underset{\|}{\|}}}C$$

B. Synthesis 310 mg of 3-bromo-1,2-propanediol (2 mmol) in 3 mol of dioxane was mixed with 240 µl (3 mmol) of 1-methylimidazole. The reaction mixture was stirred for 16 hours at 70° C. 1.36 ml (5 mmol) of myristoyl chloride and 810 µl of pyridine (10 mmol) was added to this mixture and the reaction was continued for another 24 hours at 70° C. with stirring. Dioxane was evaporated from the reaction mixture under vacuum and the residue was re-crystallized twice from hot acetonitrile. Yield 1.0 g (87% of theor.) of white powder with:

Melting point 59°±1° C.

$R_f$=0.45 in the system [1]-dichloromethane/methanol ratio 9/1.

$R_f$=0.75 in the system [2]-dichloromethane/methanol ratio 8/2. TLC plates-Kieselgel 60F$_{254}$ from EM-science.

IR: 2920, 2855 (alkane); 1245, 663 (1-methylimidazole ring); 1727, 1168 (ester)

Compound 4

A. Structure $$CH_3(CH_2)_{14}-\overset{O}{\overset{\|}{C}}-O-CH_2$$
$$CH_3(CH_2)_{14}-\overset{\|}{\underset{O}{C}}-O-CH$$
$$CH_2-S-C\underset{\underset{CH_3}{N}}{\overset{N}{\underset{\|}{\|}}}C$$

B. Synthesis 136 mg (0.2 mmol) of 1,2-dipalmitoyl-3-iodo-rac-3-deoxyglycerol was dissolved in 2 ml of dioxane and mixed with 25.1 mg (0.22 mmol) of 2-mercapto-1-methylimidazole dissolved in 2 ml of dioxane. The reaction mixture was stirred for 16 hours at 70° C. After the dioxane was evaporated, the residue was dissolved in chloroform and mixed with an equal volume of double-distilled water. After centrifugation and separation, the water layer was discarded. This extraction with water was repeated three more times. Chloroform was evaporated and the residue was dried under vacuum overnight. Yield 88 mg (66% of theor.) of white crystals with:

Melting point 53°±1° C.

$R_f$=0.20 in the system [1]-dichloromethane/methanol ratio 9/1.

$R_f$=0.60 in the system [3]-dichloromethane/methanol ratio 6/4. TLC plates-Kieselgel 60F$_{254}$ from EM-science.

IR: 2919, 2851 (alkane); 1246, 663 (1-methylimidazole ring); 1741, 1163 (ester)

Compound 5

A. Structure

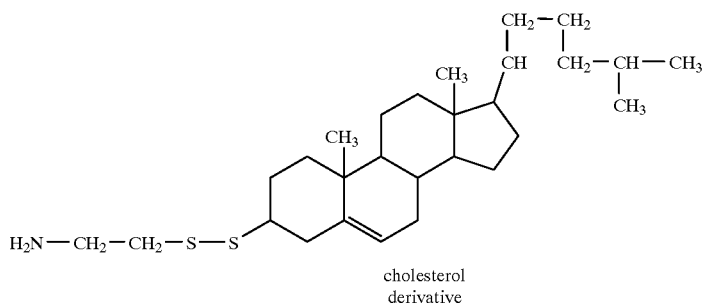

cholesterol derivative

B. Synthesis

Title Compound 5 was prepared in two steps. The first step involved synthesis of a precursor, designated Compound 5a. The structure of precursor Compound 5a is shown below.

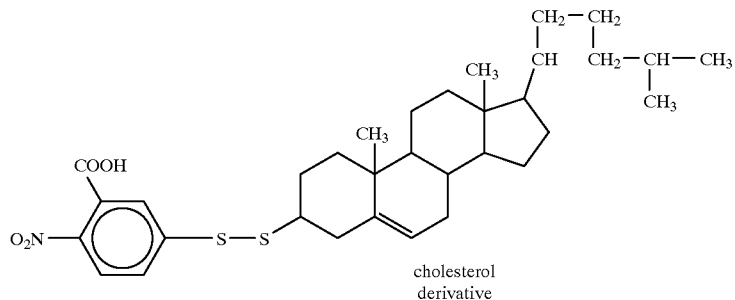

cholesterol derivative 403 mg of 3-thiocholesterol (1 mmol) solution in 10 ml of tetetrahydrofuran was mixed with 10 ml of a water solution containing 436 mg (1.1 mmol) of 5,5'-dithiobis(2-nitrobenzoic acid) in the 0.1M bicarbonate buffer, pH=7.5. After 2 hours of stirring at room temperature, a yellow precipitate of crude Compound 5a was collected as a filtrate, rinsed twice with double-distilled water, and dissolved into chloroform. The chloroform layer was extracted five times with an equal volume of double-distilled water. The water layers were combined and discarded. After the chloroform layer was evaporated, Compound 5a was dried under vacuum over night.

Yield of Compound 5a was 546 mg (91% of the theor.) of light yellow powder with:

Melting point 189°±1° C.

$R_f$=0.50 in the system [1]-dichloromethane/methanol ratio 9/1.

$R_f$=0.70 in the system [2]-dichloromethane/methanol ratio 8/2. TLC plates-Kieselgel $60F_{254}$ from EM-science.

IR: 1465, 1372 (cholesterol); 1564 (nitro group)

60 mg (0.1 mmol) of precursor Compound 5a dissolved in 5 ml of tetrahydrofuran was mixed with 14 mg (0.12 mmol) of 2-aminoethanethiolhydrochlotide (cysteamine) dissolved in 1 ml of 0.1M bicarbonate buffer (pH=7.4). After 2 hours of stirring at room temperature, tetrahydrofuran was evaporated under vacuum. The residue was mixed with 1 ml of chloroform and the chloroform solution was extracted five times with an equal volume of double distilled water. Water layers were combined and discarded. The chloroform was evaporated and Title Compound 5 was dried under vacuum over night. Yield 45.4 mg (95% of theor.).

Melting point 170° C.±1° C.

$R_f$=0.50 in the system [1]-dichloromethane/methanol ratio 9/1.

$R_f$=1.00 in the system [2]-dichloromethane/methanol ratio 8/2. TLC plates-Kieselgel $60F_{254}$ from EM-science.

IR: 2931, 2868 (alkane); 3404, 823 (amine primary); 1464, 1377 (cholesterol)

Compound 6

A. Structure

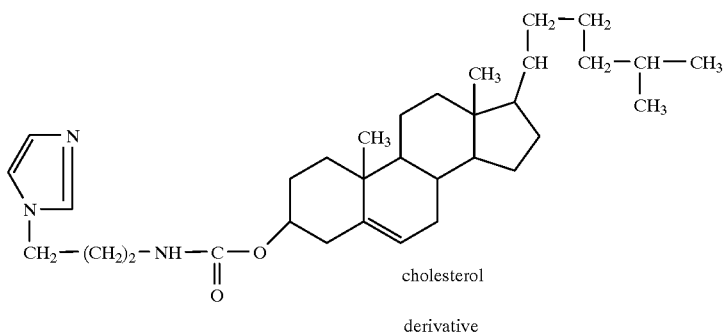

cholesterol derivative

B. Synthesis 900 mg of cholesteryl chloroformate (98%) (2 mmol) was dissolved in 10 ml of dioxane and mixed with a solution of 358 μl of 1-(3-aminopropyl)imidazole (3 mmol) in 5 ml of acetonitrile. The reaction mixture was stirred at 70° C. for 16 hours. Then, after cooling, precipitate was collected as a filtrate, rinsed with acetonitrile twice and re-crystallized from the mixture of chloroform-acetonitrile (1 volume:7 volume). Yield was 1021 mg (95% of theor.).

Melting point 172°±1° C.

$R_f$=0.62 in the system [1]-dichloromethane/methanol ratio 9/1.

$R_f$=1.00 in the system [2]-dichloromethane/methanol ratio 8/2. TLC plates-Kieselgel $60F_{254}$ from EM-science.

IR: 2947, 2870 (alkane); 1249, 664 (1-methylimidazole ring); 3109, 1640 (amide, secondary); 1466, 1380 (cholesterol)

Compound 7

A. Structure

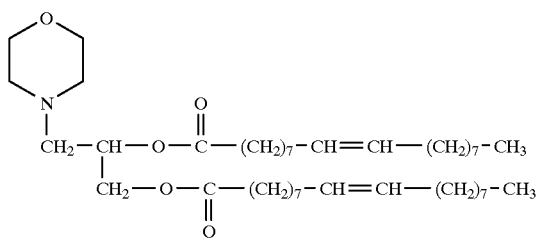

B. Synthesis 161 mg (1 mmol) of 3-morpholino-1,2-propanediol was dissolved in 3 ml of dioxane and mixed with 900 mg of oleoyl chloride (~3 mmol) and 160 μl of pyridine (~2 mmol). The reaction mixture was stirred at 70° C. for 16 hours. The dioxane was then evaporated under vacuum and the residue was dissolved in a mixture of dichloromethane/methanol (ratio 2/1 in volume). The dichloromethane was slowly evaporated from the solution under vacuum in a rotary evaporator. Title Compound 7 was crystallized from methanol with yield 655 mg (95% from theor.).

Melting point 38±1° C.

$R_f$ system [1]=0.80; $R_f$ system [2]=1.00

IR: 2931, 2868 (alkane); 1640, 960 (alkene); 1742, 1185 (ester); 1450, 1280 (N-alkylmorpholine ring)

Compound 8

A. Structure

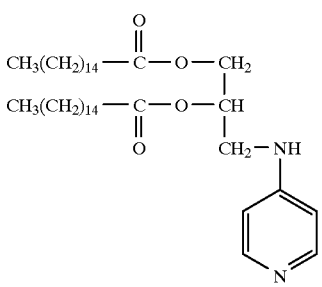

B. Synthesis 136 mg (0.2 mmol) of 1,2-dipalmitoyl-3-iodo-rac-3-deoxyglycerol was dissolved in 3 ml of dioxane and mixed with 206 mg (0.22 mmol) of 4-aminopyridine. The reaction mixture was stirred for 16 hours at 70° C. Dioxane was evaporated under vacuum and the residue was recrystallized twice from the hot acetonitrile. Yield-130 mg (84% of the theor.) of Title Compound 8 with:

Melting point 141±1° C.

$R_{f/system1}$=0.40; $R_{f/system2}$=0.62

IR: 2918, 2849 (alkane); 1741, 1173 (ester); 1644, 1447 (4-aminopyridine ring)

Compound 9

A. Structure

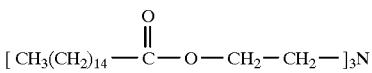

B. Synthesis 150 mg (~1 mmol) of triethanolamine was mixed with 5 ml of dioxane and 990 mg (3.6 mmol) of palmitoyl chloride. The reaction mixture was stirred for 16 hours at 70° C. Dioxane was evaporated under vacuum, the residue was dissolved in a mixture of dichloromethane/methanol (ratio 2/1) and dichloromethane was slowly evaporated from solution under vacuum in a rotary evaporator. Title Compound 9 was crystallized from methanol with yield of 787 mg (91% of the theor.)

Melting point 40±1° C.

$R_{f/system1}$=0.37; $R_{f/system2}$=0.83

IR: 2917, 2851 (alkane); 1739, 1177 (ester)

Compound 10

A. Structure

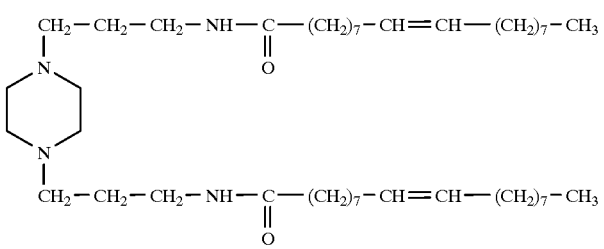

B. Synthesis 200 mg (1 mmol) of 1,4-Bis(3-aminopropyl)piperazine was dissolved in 5 ml of dioxane and mixed with 722 mg (2.2 mmol) of oleoyl chloride. The reaction mixture was stirred 16 hours at 70° C. and dioxane was evaporated under vacuum. The residue was dissolved in a mixture of dichloromethane and methanol (ratio 2/1) and dichloromethane was slowly evaporated under reduced pressure in a rotary evaporator. Title Compound 10 was crystallized with yield of 634 mg (87% of the theor.) with:

Melting point 224±1° C.
$R_{f/system1}$=0.30; $R_{f/system2}$=0.80
IR: 2925, 2854 (alkane); 1635, 960 (alkene); 3076, 1641 (amide, secondary); 1466, 825 (piperazine ring)

Compound 11

A. Structure

B. Synthesis 47.5 mg (0.1 mmol) of N-Hydroxysuccinimidyl-9-fluoro-16α-methyl-11β, 17 dihydroxy-3-oxo-1,4-androstadiene-17β-carboxylic acid was dissolved in 1 ml of acetonitrile and mixed with 15 mg (0.12 mmol) of 1-(3-aminopropylimidazole). N-hydroxysuccinimidyl-9-fluoro-16α-methyl-11β, 17-dihydroxy-3-oxo-1,4-androstadiene-17β-carboxylic acid can be made by methods well known to those skilled in the art. (See, for example, M. V. Govindan et al., *Eur. J. Biochem.* 108, pp. 47–53, 1980.) The reaction mixture was stirred for 16 hours at 50° C. After cooling the solution to 4° C., crystallized Title Compound 11 was separated by centrifugation and re-crystallized from hot acetonitrile. Yield 43 mg (85% from the theor.)

Melting point: (destruction at 230° C.)
$R_{f/system1}$=0.20; $R_{f/system2}$=0.80
IR: 2921, 2855 (alkane); 1242, 665 (1-methylimidazole ring); 2975, 1640 (amide, secondary); 1685, 897 (dexamethazone)

Compound 12

A. Structure

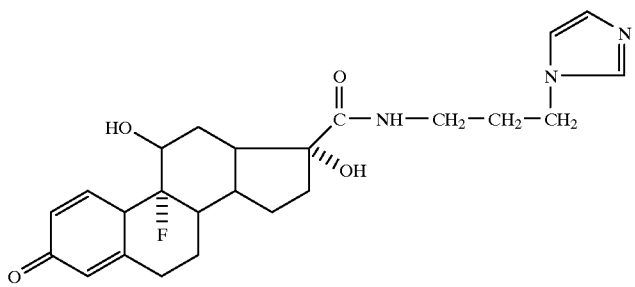

Dexamethasone Derivative

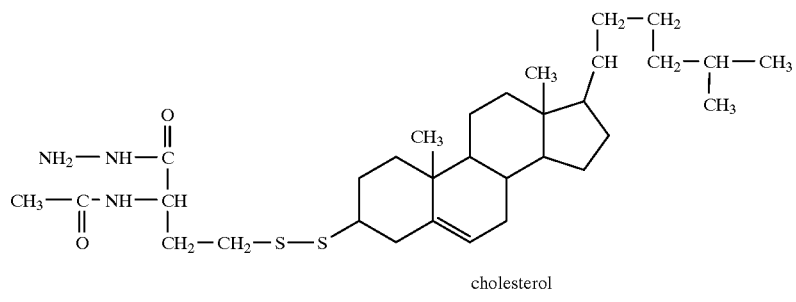

cholesterol derivative

B. Synthesis 60 mg of compound 5a (0.1 mmol) in 3 ml of tetrahydrofuran was mixed with 35 mg (0.2 mmol) of 2-acetamido-4-mercaptobutyric acid hydrazide in 2 ml of a 5% solution of sodium bicarbonate (pH 8.0) and then the reaction mixture was stirred at room temperature overnight while being protected from direct light. 2-acetamido-4-mercaptobutyric acid hydrazide may be synthesized using procedures well known to those in the art. (See, for example, K. E. Taylor et al., *Biochemistry International* 1 (4), pp. 353–358, 1980.) The precipitate was filtered and rinsed with double distilled water until all traces of yellow color was removed (λmax=412 nm). The title compound 12 was collected from the filter and dried under vacuum overnight. The yield was 37 mg (64% of the theoretical yield) of slightly reddish crystals. An additional 20% of theoretical yield of compound 12 can be purified from the filtrates.

Melting Point=188° C.±1° C.
$R_f$=0.20 in system [1]
$R_f$=0.90 in system [2]
IR: 2935, 2867 (alkane); 3480, 1600 (amine, primary); 3082, 1333 (amide, secondary); 1464, 1379 (cholesterol)

Compound 13

A. Structure

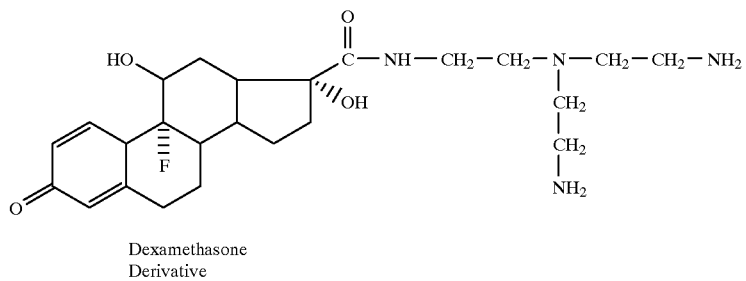

Dexamethasone Derivative

B. Synthesis 47.5 mg (0.1 mmol) of N-hydroxysuccinimidyl-9-fluoro-16α-methyl-11β, 17-dihydroxy-3-oxo-1,4-androstadiene-17β-carboxylic acid was dissolved in 1 ml of acetonitrile and mixed with 75 µl (0.5 mmol) of tris (2-aminoethyl) amine. N-hydroxysuccinimidyl-9-fluoro-16α-methyl-11β, 17-dihydroxy-3-oxo-1,4-androstadiene-17β-carboxylic acid can be made by methods well known to those skilled in the art. (See, for example, M. V. Govindan et al., *Eur. J. Biochem.* 108, pp. 47–53, 1980.) The reaction mixture was stirred at 50° C. for 16 hours, acetonitrile was evaporated and the residue was dissolved in chloroform. The chloroform layer was mixed with water (1/5 of chloroform volume). After centrifugation and separation, the water layer was extracted four more times with chloroform. The chloroform layer was evaporated under vacuum and the residue was recrystallized from acetonitrile at 4° C. Yield was 34 mg (~68% of theoretical). Title Compound 13 was a white crystal with melting point of 81° C.±1° C. $R_f$=0.00 in system [1], Rf=0.36 in system [8].

IR: 2956, 2871 (alkane); 3419, 838 (amine, secondary); 2956, 1663 (amide, secondary); 1695, 912 (dexamethazone)

Compound 14

A. Structure

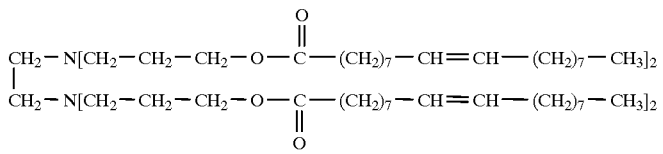

B. Synthesis 29 mg (0.1 mmol) of N,N,N'N'-tetrakis(2-hydroxypropyl) ethylene-diamine was dissolved in 2 ml of dioxane and mixed with 150 mg (~0.5 mmol) of oleoyl chloride and 65 mg of N,N-diisopropylethylamine (0.5 mmol). The reaction mixture was stirred for 16 hours at 70° C. and Title Compound 14 was purified by preparative TLC on silica gel 60F-254 TLC plates with dichloromethane as an eluent. Yield 78.3 mg (58% of the theoretical)

Melting point 38±1° C.

$R_f/_{system}$=0.75; $R_f/_{system1}$=1.00; $R_f/_{system2}$=1.00

IR: 2938, 2870 (alkane); 1661, 973 (alkene); 1741, 1178 (ester)

Compound 15

A. Structure

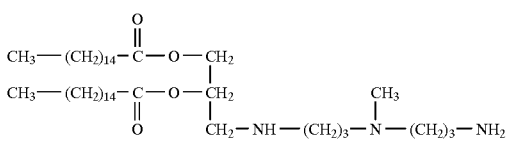

B. Synthesis 136 mg (0.2 mmol) of 1,2-dipalmitoyl-3-iodo-2rac-3-deoxyglycerol was dissolved in 3 ml dioxane and mixed with 48 µl (0.3 mmol) of 3,3'-diamino-N-methyldipropylamine. The reaction mixture was stirred during 16 hours at 70° C., dioxane was evaporated under vacuum and the residue dissolved in chloroform and mixed with water (1/5 of chloroform volume). After centrifugation and separation, the water layer was discarded and the extraction was repeated four more times. The chloroform layer was evaporated under vacuum and the residue was recrystallized from acetonitrile. Yield was 112 mg (68% of theoretical) of white crystals with melting point of 37° C.±1° C. Rf of 0.40 in system [1] and 0.75 in system [5].

IR: 2926, 2855 (alkane); 1740, 1180 (ester); 3430, 803 (amine, primary); 3380, 1172 (amine, secondary)

Compound 16

A. Structure

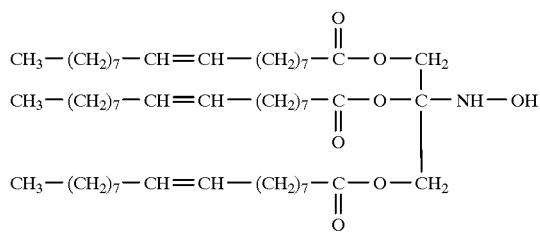

B. Synthesis

Title Compound 16 was prepared in two steps. The first step involved preparation of precursor Compound 16a, the structure of which is shown below.

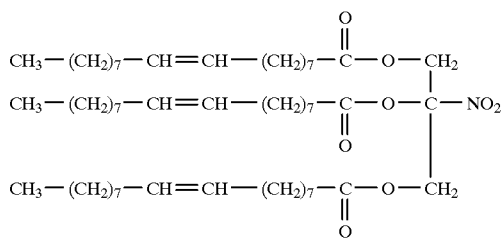

1.51 g of tris (hydroxymethyl)nitro methane (10 mmol) was mixed with 11.6 ml of oleic acid (90%) (33 mmol), 10 g of ion exchange resin Dowex 50X2-100 (H+ form) and 100 ml of dry benzene. The reaction mixture was boiled in a conical flask with a Dean-Stark receiver for 48 hours. The ion exchange resin was filtered and discarded. Benzene was evaporated from the filtrate under vacuum. The residue was dissolved in chloroform and the chloroform layer was mixed with equal volume of 3% solution of sodium bicarbonate (pH 7.5) in water. After centrifugation, the water layer and interphase were discarded, the chloroform layer was rinsed twice with water and the chloroform was evaporated under vacuum. Yield of Compound 16a was 6.8 g (72 % of theoretical). The product was light yellow and liquid at room temperature, with a $R_f$ of 0.65 in system [1] and 1.00 in system [2].

IR: 2925, 2854 (alkane); 1639, 967 (alkene); 1711, 1192 (ester); 1551. 1378 (nitro group)

945 mg of Compound 16a from above (1 mmol) was dissolved in 10 ml of absolute ethanol and to that solution was added 125 mg of sodium cyanoborohydride ( 2 mmol) slowly over 10 minutes. The reaction mixture was stirred at room temperature during two hours. Then the temperature was raised to 70° C. and the reaction mixture was stirred at 70° C. for another 16 hours. The ethanol was evaporated under vacuum and the residue was distributed between chloroform and water. After centrifugation and separation, the water layer was discarded and the extraction procedure was repeated four more times. The chloroform layer was evaporated under vacuum. Yield of Title Compound 16 was 828 mg (89% of theoretical). Melting point 29° C.±1° C. Rf of 0.60 in system [1] and 1.00 in system [2].

IR: 2927, 2855 (alkane); 1641, 967 (alkene); 1712, 1185 (ester); 1552, 723 (alkylhydroxylamine); 3330, 1042 (hydroxyl)

Compound 17

A. Structure

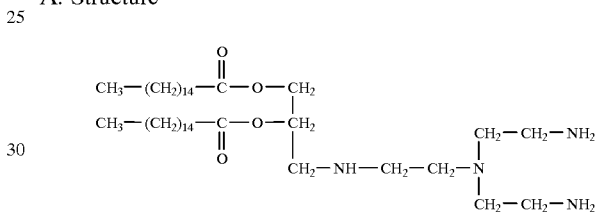

B. Synthesis 136 mg (0.2 mmol) of 1,2-dipalmitoyl-3-iodo-rac-3-deoxy-glycerol was dissolved in 2 ml of dioxane and mixed with 55 µl (0.3 mmol) of tris (2-aminoethyl) amine and 100 µl (~0.3 mmol) of N,N-diisopropylethylamine. The reaction mixture was stirred for 48 hours at 70° C., dioxane was evaporated under vacuum, and the residue was dissolved in chloroform and mixed with water (½ volume of chloroform). After centrifugation and separation, the water layer was discarded and the extraction was repeated four more times. The chloroform was evaporated under vacuum and the residue was re-crystallized from ethanol. Yield was 137 mg (83% of theoretical). The white powder had a melting point of 48° C.±1° C. $R_f$ of 0.00 in system [2] and $R_f$ of 0.70 in system [6].

IR: 2922, 2853 (alkane); 1727, 1165 (ester); 3420, 810 (amine, primary); 3322, 1113 (amine, secondary)

Compound 18

A. Structure

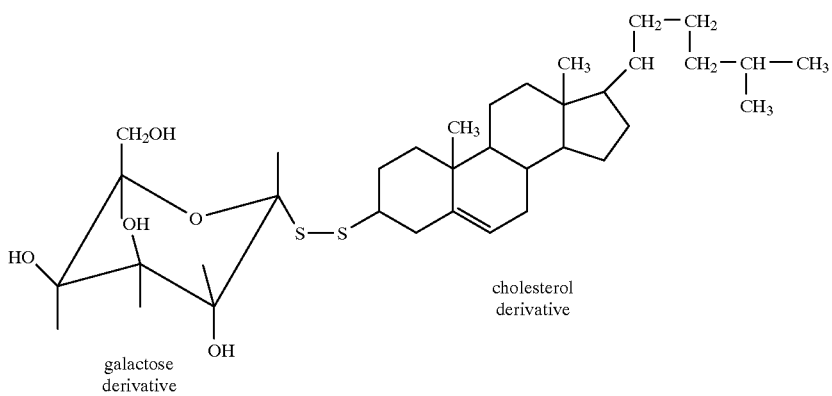

B. Synthesis 60 mg of the compound 5a (0.1 mmol) in 3 ml of tetrahydrofuran was mixed with 65 mg (0.3 mmol) of the sodium salt of 1-thio-β-d-galactopyranose (Sigma Chemical) in 2 ml of a 5% solution of sodium bicarbonate (pH 8.0) and the reaction mixture was stirred at room temperature overnight wile being protected from direct light. Then, the precipitate was filtered and rinsed with water until all traces of yellow color was removed (λmax=412 nm). The title compound 18 was collected from the filter and dried under a vacuum overnight. The yield was 33 mg (55% of theoretical yield) of white crystals. An additional 25% of the compound can be purified from the combined filtrates. Melting point of 198° C.±1° C., $R_f$ of 0.40 in system [1] and $R_f$ 1.00 in system [2].

IR: 2936, 2868 (alkane); 1465, 1380 (cholesterol); 1437, 1085 (thiogalactopyranose)

Compound 19

A. Structure

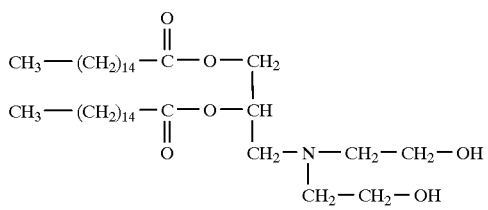

B. Synthesis 136 mg (0.2 mmol) of 1,2-dipalmitoyl-3-iodo-rac-3-deoxyglycerol was dissolved in a mixture of 2 ml of acetonitrile and 3 ml of dioxane, mixed with 100 μl (~1 mmol) of diethanolamine and stirred for 16 hours at 50° C. The dioxane and acetonitrile were evaporated under vacuum, the residue was dissolved in chloroform and the chloroform layer was mixed with water (1/2 volume of chloroform). After centrifugation and separation, the water layer was discarded and the extraction was repeated four more times. The chloroform layer was evaporated under vacuum and the residue was re-crystallized from acetonitrile (at 4° C.). Yield was 113 mg (86% of theoretical) of white powder with uncorrected melting point of 39±1° C. Rf is system [1] 0.62 and Rf in system [2] 1.00.

IR: 2924, 2854 (alkane); 1741, 1182 (ester); 3380, 1073 (hydroxyl)

Compound 20

A. Structure

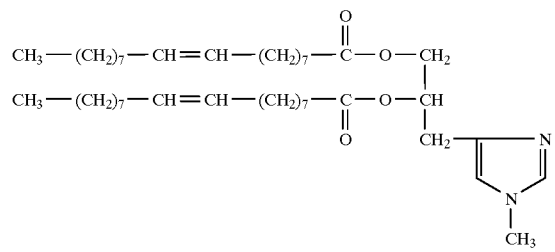

B. Synthesis 310 mg of 3-bromo-1,2-propanediol (2 mmol) in 3 ml of dioxane was mixed with 800 μl (10 mmol) of 1-methylimidazole. The reaction mixture was stirred for 16 hours at 70° C., mixed with 1945 μl (~5 mmol) of oleoyl chloride (85%). Stirring was continued for another 24 hours at 70° C. The dioxane was evaporated under vacuum and Title Compound 20 was purified by flash chromatography (column 25×300 mm, Silica Gel G (Merck) 75–140 μm elution by step gradient of methanol in chloroform, TLC control: system 2: dichloromethane/methanol-ratio 8/2). Yield of Title Compound 20 (eluted at ratio of 95/5) was 1,118 mg (~73% of theoretical) as a light yellow liquid. Rf in system [1] 0.30 and Rf in system [2] 0.80.

IR: 2926, 2855 (alkane); 1641, 962 (alkene); 1241, 622 (1-methylimidazole ring); 1742, 1170 (ester)

Compound 21
A. Structure

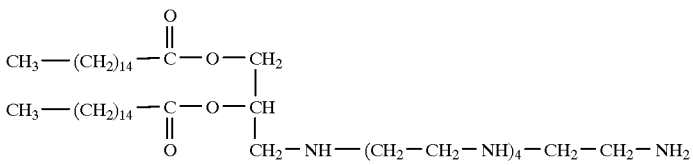

B. Synthesis 136 mg (0.2 mmol) of 1,2-dipalmitoyl-3-iodo-rac-3-deoxyglycerol was dissolved in 2 ml of dioxane and mixed with 74 µl (0.3 mmol) of pentaethylenehexamine. The reaction mixture was stirred for 16 hours at 70° C., the dioxane was evaporated under vacuum, the residue was dissolved in chloroform and the chloroform layer was mixed with water (1/5 volume of chloroform). After centrifugation, the water layer was separated and discarded and the extraction procedure was repeated four more times. The chloroform layer was evaporated under vacuum and the residue was crystallized from acetonitrile. Yield of Title Compound 21 was 98.5 mg (54%) as a white powder with melting point of 28° C.±1° C., Rf of 0.00 in system [2] and 0.78 in system [6],.

IR: 2925, 2854 (alkane); 1740, 1190 (ester); 3577, 1600 (amine, primary); 3292, 1119 (amine, secondary)

Compound 22
A. Structure

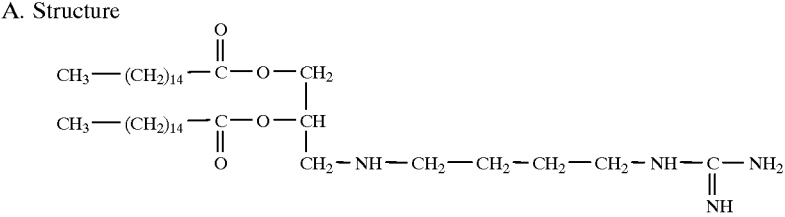

B. Synthesis 136 mg (0.2 mmol) of 1,2-dipalmitoyl-3-iodo-rac-3-deoxyglycerol was dissolved in 3 ml of dioxane and mixed with 68.5 mg (0.3 mmol) of (4-aminobutyl)guanidine sulfate (agmatine sulfate) and 52 µl (0.3 mmol) of N,N-diisopropylethylamine. Then, the reaction mixture was stirred at 70° C. overnight (16 hours) while being protected from direct light. The title compound was crystallized from the reaction mixture (at 4° C.), rinsed three times with 200 µl of cold acetonitrile and dried under vacuum overnight. The yield of compound 22 was 96 mg (70% of theoretical yield). Melting point of 85° C.+1° C., Rf of 0.40 in system [1] and Rf of 0.72 in system [2].

IR: 2954, 2918 (alkane); 1741, 1198 (ester); 3459, 1602 (amine, primary); 3382, 1118 (amine, secondary); 3056, 1310 (amide, secondary or guanidine)

Compound 23
A. Structure

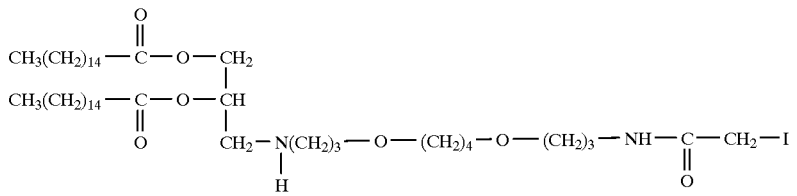

B. Synthesis

A solution of 75.6 mg of compound 2 (0.1 mmol) in 4 ml of chloroform was mixed with 20.5 mg (0.11 mmol) of iodoacetic acid, 61.8 mg (0.3 mmol) of 1,3-dicyclohexylcarbodiimide and 35 µl (0.2 mmol) of N,N-diisopropylethylamine. The reaction mixture was stirred 24 hours at room temperature while being protected from direct light and then mixed with 100 µl of water and stirred an additional two hours. The precipitate was filtered, rinsed twice with 200 µl of chloroform and discarded. The combined filtrates were mixed with 1 ml of water and the two layers were separated by centrifugation. The water layer was discarded and then the operation was repeated four more times. The chloroform layer was dried over anhydrous magnesium sulfate and evaporated under a vacuum. The title compound 23 was finally purified by preparative thin layer chromatography (system [1]) on TLC-plates-Kieselgel 60F254 from EM science. The yield was 72 mg (76% theoretical yield). Melting point of 150° C.+2° C., Rf of 0.54 in system [1] and Rf of 1.00 in system [2].

IR: 2924, 2854 (alkane); 1740, 1200 (ester); 1100 (ether); 3350, 1120 (amine, secondary); 3080, 1316 (amide, secondary)

Compound 24

A. Structure

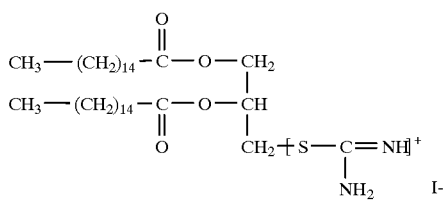

B. Synthesis 136 mg (0.2 mmol) of 1,2-dipalmitoyl-3-iodo-rac-3-deoxyglycerol was dissolved in 3 ml of dioxane and mixed with 46 mg (about 0.6 mmol) of thiourea in 1 ml of ethanol. The reaction mixture was then stirred for 16 hours at 50° C. while being protected from direct light. Then, the reaction mixture was left for 4 hours at 4° C. A white precipitate was then filtered, rinsed three times with cold acetonitrile (4° C.), three times with water (4° C.) and dried under a vacuum overnight. The yield of the title compound 24 (as white crystals) was 95 mg (63% of the theoretical yield). An additional 20 mg can be purified from the filtrate. Melting point of 85° C.±1° C., Rf of 0.00 in system [2], Rf=0.72 in system [8].

IR: 2917, 2850 (alkane); 1735, 1222 (ester); 3505, 1600 (amine, primary); 3268, 1121 (amine, secondary); 3082, 1320 (amide secondary or thiuronium)

Compound 25

A. Structure

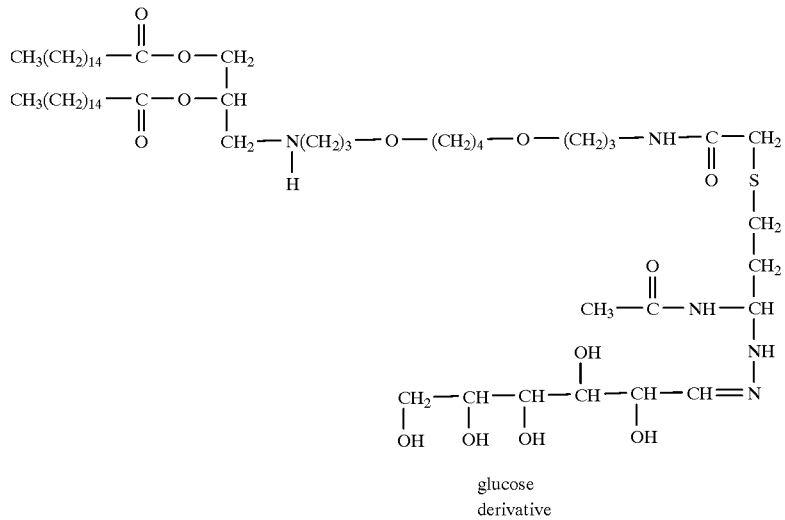

B. Synthesis

A solution of 17.5 mg (0.1 mmol) of 2-acetamide-4-mercaptobutyric acid hydrazide and 54 mg (0.3 mmol) of α-d-glucose in 2 ml of water was stirred for 4 hours at room temperature. To that reaction mixture was added a solution of 47 mg (0.05 mmol) of compound 23 and 18 μl (0.1 mmol) of N,N-diisopropylethylamine in 3 ml of dioxane. Then, the reaction mixture was stirred at 37° C. for an additional 20 hours (protected from direct light), dioxane and water were evaporated under vacuum and the precipitate was distributed between chloroform (3 ml) and a 1/1 ratio mixture of water and methanol (2 ml). The top layer was separated by centrifugation. The chloroform layer was rinsed 4 more times with 2 ml (each time) of the 1/1 mixture of water and methanol mixture. Then, the chloroform was evaporated and the white precipitate obtained was dried under vacuum overnight at 40° C. The yield of the title compound 20 was 31 mg (54% of the theoretical yield). An additional amount of compound 20 can be purified from the combined water and methanol layers. Melting Point of 38° C.+1° C. $R_f$ of 0.00 in system [2] and $R_f$ of 0.49 in system [7].

IR: 2916, 2850 (alkane); 1738, 1223 (ester); 1102 (ether); 3360, 1119 (amine, secondary); 3086, 1324 (amide, secondary); 3332, 1080 (hydroxyl)

EXAMPLE 2

Compound 3 Containing Liposomes Become More Fusogenic With Decreasing pH

Preparation of Liposome Formulations

Liposomes were prepared by mixing chloroform solutions of the different lipids in microcentrifuge tubes at 1.5 ml and removing the chloroform by vacuum to produce dried lipid films. Tubes were placed under vacuum overnight to remove solvent traces. The amounts of cationic lipids in all cases were 1.34 mmol/ml with different amounts of other lipids as specified. One ml of sterile 10 mM HEPES buffer pH 7.8 was added, and the tubes were sealed and vortexed for 1 min at room temperature and then sonicated in to obtain a clear emulsion.

Methods for Determining Vesicle-Vesicle Fusion

To those well-skilled in the art, vesicle-vesicle fusion can be detected by measuring fluorescence resonance energy transfer (RET) between two lipid analogs originally placed in the same liposomes. When the two lipid analogs are in close proximity the emission of one fluorescent compound can excite another fluorescent compound. When the liposome containing the two lipid fluorescent analogs fuses with liposomes that do not contain any fluorescent analogs, the fluorescent analogs are diluted out and the resonance energy transfer is reduced. The present study used the RET system comprised of the energy donor, N-NBD-DPPE (N-(7-nitro-2,1,3-benzoxadiazol-4-yl)phosphatidylethanolamine) which has a $\lambda_{ex}$=467 nm and a $\lambda_{em}$=534 nm and the energy acceptor, N-Rh-PE (N-(lissamine rhodamine B sulfonyl) phosphatidylethanolamine), which has a $l_{ex}$=560 nm and a $\lambda_{em}$=585 nm.

The liposomes, which consist of a) Compound 1 1.34 mM, DOPE 1.36 mM, N-NBD-DPPE 0.026 mM, N-Rh-DPPE 0.026 mM and b) Compound 1 1.34 mM, phosphatidylcholine 1.26 mM, N-NBD-DPPE 0.026 mM, N-Rh-DPPE 0.026 mM were prepared in 10 mM HEPES pH 8.1 as described above. Steady-state emission spectra were obtained by using a spectrofluorimeter. The value of excitation was 470 nm. The kinetic of fusion between vesicles containing fluorescent lipids (both N-NBD-PE and N-Rh-PE) and vesicles devoid of fluorescent lipid was measured by changes in fluorescence intensity at 530 nm to determine the degree of quenching as the result of RET. The reaction mixture contained 6-fold excess of unfluorescent liposomes. The final lipid concentration was 80 µM. Following each measurement, vesicles were disrupted with Triton X-100 (1% final concentration). The fluorescence level thus obtained was set at 100% of fusion.

Studies were performed as described above. About 5 µl of fluorescent liposomes were added to 1 ml of buffer solution. Fusion was initiated by the addition of 10 µl of non-fluorescent liposomes. In experiments with DNA, 5 µg of pBS.RSVLux plasmid DNA were added to fluorescent liposomes in different buffers and mixtures were incubated 15 min. at room temperature before addition of non-fluorescent liposomes. The results are summarized in Table 1. Table 1 shows the dependence of initial rates of fusion of Compound 1//DOPE liposomes as a function of solution pH.

TABLE 1

| pH[1] | $V_{in.}$ (%/min.) | $V_{in.}$ (%/min.) in presence of DNA |
|---|---|---|
| 3.54 (20 mM NaAc) | 14.0 | |
| 4.57 (20 mM NaAc) | 15.0 | |
| 5.30 (20 mM NaAc) | 16.5 | |
| 5.85 (20 mM NaAc) | 16.0 | |
| 6.40 (20 mM HEPES) | 17.0 | 20.0 |
| 6.86 (20 mM HEPES) | 20.0 | 22.0 |
| 7.40 (20 mM HEPES) | 16.0 | 10.4 |
| 7.90 (20 mM HEPES) | 6.0 | 1.4 |
| 8.35 (20 mM HEPES) | 4.7 | 1.0 |
| 8.80 (20 mM Gly) | 3.7 | |
| 9.10 (20 mM Gly) | 5.4 | |

[1]All buffers contain 150 mM NaCl.

The data in Table 1 show that Compound 1 containing liposomes either with or without DNA have increasing fusion with decreasing pH.

EXAMPLE 3

Methods for Determination of Leakage of Liposomes

Lissamine Rhodamine B (Kodak) containing liposomes were prepared as follows. A dry lipid mixture of 2.68 mmol of Compound 1 and 2.52 mmol of phosphatidylcholine were dispersed in 1 ml of aqueous 25 mM Lissamine Rhodamine solution (pH 7.4) and sonicated for 20 min. Free Lissamine Rhodamine was removed by gel chromatography on a Sephadex G-25 column by using 10 mM HEPES buffer pH 8.1 containing 125 mM NaCl and 0.1 mM EDTA. Lissamine Rhodamine -loaded liposomes were dispersed in different buffers of preadjusted pH. All buffers contained 0.125 mM NaCl. Excitation and monitoring wavelengths of Lissamine Rhodamine were 560 nm and 590, respectively. The percent leakage of liposomes was defined as % leakage=$(F_t-F_0)/(F_f-F_0) \times 100$, where $F_O$ and $F_t$ are the initial and intermediate fluorescence intensities respectively. $F_f$ is the fluorescence intensity after addition of Triton X-100 (final concentration 1%). The results are summarized below in Table 2. Table 2 shows the effect of pH on the Lissamine Rhodamine leakage rate from Compound 1/phosphatidylcholine and phosphatidylcholine liposomes. 10 µl of Compound 1/PE liposome with concentration of Compound 1 1.34 mM and phosphatidylcholine 1.24 mM or phosphatidylcholine liposomes (concentration 2.48) were added to 1 ml of different buffers. In some experiments 10 µg of pBS.RSVLux plasmid DNA were added to solutions immediately after liposomes were added to different buffers. Leakage was defined as described above.

TABLE 2

| Buffer* | Compound 1/Phosphatidylcholine | Compound 1/Phosphatidylcholine + DNA | Phosphatidylcholine |
|---|---|---|---|
| Gly pH 10.0 | 0.53 | 0.8 | |
| Gly pH 9.0 | 0.27 | 0.8 | |
| Tris pH 8.0 | 0.13 | 0.8 | 0.2 |
| Tris pH 7.5 | 0.27 | 0.8 | |
| Tris pH 7.0 | 0.27 | 1.07 | 0.2 |
| Tris pH 6.5 | 0.53 | 1.47 | |
| NaAc pH 6.0 | 0.67 | 2.0 | 0.25 |
| NaAc pH 5.4 | 1.07 | 2.9 | |
| NaAc pH 4.8 | 8.53 | 12.5 | 0.35 |
| NaAc pH 4.3 | 11.2 | 21.3 | 0.45 |
| NaAc pH 3.8 | 17.3 | 20.0 | 1.05 |

*All buffers contain 20 mM buffer component and 125 mM NaCl.

The data in Table 2 show that the Compound 1 containing liposomes, either with or without DNA, have increasing leakage with decreasing pH.

EXAMPLE 4

Decreasing pH Increases Binding of DNA to Compound 1/Phosphatidylcholine Liposomes Liposomes were prepared in water as described above in Example 2. The concentration of Compound 1 was 2.68 mM and the concentration of phosphatidylcholine was 2.48 mM. Plasmid pBS.RSVLux DNA was used. The reaction mixture contained 1 ml 0.01M Tris, 0.15M NaCl (adjusted to the specified pH) and either:

a) low amount of liposome-24 µg of DNA and 50 µg of liposomes, or b) high amount of liposome-20 µg DNA and 150 µg of liposomes.

After 10 min incubation at room temperature, the solution was spun at 15,000 rpm for 10 min. 200 µl of supernatant were collected and added to 1 ml of 0.02M Tris, 0.15M NaCl pH 7.5. Ethidium bromide was added to a concentration of 0.1 mM. The fluorescence was determined with a spectrophotometer at 526-nm excitation and 590-nm emission. The concentration of free DNA was determined from comparison with fluorescence of standard solutions with different DNA concentration. The results are summarized in Table 2a.

TABLE 2A

| | Free DNA (%) | |
|---|---|---|
| pH | Low Amount of Liposomes | High Amount of Liposomes |
| 5.5 | 4 | — |
| 6 | 4.5 | 1.5 |
| 6.5 | 7.5 | 1 |
| 7 | 17.5 | 2 |
| 7.5 | 21 | 2 |

TABLE 2A-continued

| | Free DNA (%) | |
|---|---|---|
| pH | Low Amount of Liposomes | High Amount of Liposomes |
| 7.75 | 25 | 5.5 |
| 8 | 26.5 | 1.5 |
| 8.25 | 28 | 1.5 |
| 8.5 | 31.5 | 4 |
| 9 | 33 | 10 |
| 9.5 | 36 | 15 |

For the experiment using the "high amount of liposome" the percentage of free DNA was also determined. 200 μl were collected from the reaction mixture containing 20 μg of DNA and 150 μg of Compound 1/phosphatidylcholine in 0.01M Tris, 0.15M NaCl with different pH's and added to 1 ml of the same buffer with 0.1 mM ethidium bromide. The increase fluorescence at 590 nm was normalized to the fluorescence of free DNA in this buffer. The results are shown in Table 2B.

TABLE 2B

| pH | DNA Accessible to Ethidium Bromide (%) |
|---|---|
| 6 | 29 |
| 6.5 | 35 |
| 7 | 38 |
| 7.5 | 43 |
| 7.75 | 44.5 |
| 8 | 49 |
| 8.25 | 48 |
| 8.5 | 46 |
| 9 | 54 |

These results show that the amount of plasmid DNA unbound to Compound 1/phosphatidylcholine liposomes or accessible to ethidium bromide decreased with decreasing pH.

EXAMPLE 5

Plasmid DNA liposomes containing a wide ratio of lipids to plasmid DNA can mediate the transfection and expression of reports genes more efficiently than Lipofectin (DOTMA/ Dioleoylphosphatidylcholine)

Preparation of Liposome Formulations

Liposomes were prepared by mixing chloroform solutions of the different lipids in microcentrifuge tubes with a 1.5 ml and removing the chloroform by vacuum to produce the dried lipid films. Tubes were placed under vacuum overnight to remove solvent traces. The amounts of cationic lipids in all cases were 1.34 mmol/ml with different amounts of other lipids as specified. One ml of sterile 10 mM HEPES buffer, pH 7.8, was added, and the tubes were sealed and vortexed for 1 min at room temperature and sonicated to obtain a clear emulsion.

Exposure of Cells to Liposome/Plasmid Formulation

Cell Culture

The following cell lines were used: mouse 3T3 fibroblasts, COS cells (monkey kidney cell line transformed with the SV40 T ag), HeLa (human carcinoma cells), HepG2 (human hepatoma cell), 293 (monkey kidney cell line transformed with the adenovirus E1 gene) were maintained in Dulbeco's Modified MEM media supplemented with 10% fetal calf serum. All cultures were maintained in a humidified atmosphere of 5% $CO_2$ in air at 37° C. The cells were seeded in a 6-well plate (35 mm culture dishes) or a 12 well-plate (25 mm culture dishes) 24 h before the transfection at 70% confluence. Before transfection, the cells was washed once with Opti-MEM. In case of the 35 mm culture dishes, four μg of plasmid DNA (containing the luciferase or β-galactosidase reporter genes described below) in 0.75 ml of Opti-MEM was mixed with various amounts of liposomes in 0.75 ml of Opti-MEM. In case of the 25 mm culture dishes, one or two μg DNA in 400 μl of Opti-MEM was mixed with 400 μl of liposomes in 400 μl of Opti-MEM. The mixtures were incubated for 30 min at room temperature prior to being added to the cells in the culture dish. The cells were incubated at 37° C. in 5% $CO_2$/95% air. After four hours, the transfection mixture was removed and replaced with 0.75 ml and 1.5 ml of DMEM+10% FCS for 25 mm and 35 mm plates, respectively. The cultures were incubated for 24 hours until they were harvested for analysis of their reporter gene expression.

Transfections requiring only plasmid DNA and Lipofectin™ (GIBCO BRL), lipofectAMINE™ (3:1 (w:w) ratio of DOSPA which is 2,3-dioleyloxy-N-[20({2,5-bis[(3-aminopropyl)amino]-1-oxypentyl}amino)ethyl]-N,N-dimethyl-2,3-bis(9-octadecenyloxy)-1-propanaminium trifluoroacetate and DOPE) (GIBCO BRL),TransfectACE™ (1:2.5 (w:w) ratio of DDAB which is dimethyl dioctadecylammonium bromide and DOPE)(GIBCO BRL) or DOTAP (N-[1-(2,3-dioleoyloxy)propyl]-N,N,N-trimethylammoniummethylsulfate) were also prepared according to the manufacturers' recommendations.

Use of Reporter Genes

The firefly luciferase and E. coli β-galactosidase reporter genes were used to determine the efficiency of DNA transfer quantitatively. The previously described, plasmid DNA pBS.RSVLux was used to express the firefly luciferase reporter gene from the Rous Sarcoma Virus (RSV) LTR promoter. The plasmid also contains the SV40 intron and poly A addition signals for proper and efficient mRNA processing. The β-galactosidase expression plasmid, pBS.C-MVLacZ was derived from phosphatidylcholineMVb-gal by placing the CMV promoter, β-galactosidase coding sequence and the SV40 intron/poly A sequences within pBluescript KS-(Stratagene). All plasmids were purified by alkaline lysis and then two cesium chloride gradients as previously described.

Reporter Gene Assays

For determination of luciferase activity, cells were lysed by the addition of 100 ml for 25 mm plates and 200 μl for 35 mm plates of lysis buffer (0.1% Triton X-100, 0.1M K-phosphate, 1 mM DTT, pH 7.8). 20 μl of the cellular extract were analyzed for luciferase activity.

For determination of β-galactosidase activity, the cells in 12-well plate were lysed with 100 μl of 0.1% Triton X-100, 250 mM Tris, pH 8.0. 50 μl of the cell suspension was placed in wells of a 96-well plate and 150 μl of ortho-nitrophenol galactopyranoside (2 mg/ml) in 60 mM sodium phosphate pH 8.0, 1 mM $MgSO_4$, 10 mM KCl, 50 mM β-mercaptoethanol was added. After 4 hours of incubation at 37° C., optical density at 405 nm in every wall was determined in a microtiter plate reader (Dynatech MR250).

The amount of soluble protein in extracts was determined by the BCA Protein Assay Reagent (Pierce, Co., Rockford, Ill.) assay in 20 μl of extract. No DTT was used in the cellular lysis buffer when protein assays were done. The cells were also washed with normal saline three times to remove residual serum. This determination of protein concentration enabled the specific activity of reporter protein to be determined. The measurement of cellular protein was also used as indication of cellular survival following exposure to the liposome/DNA complexes and therefore indicated the toxicity of the liposome/DNA complexes.

Compound 1/DOPE (1:1 molar ratio) liposomes were prepared as described above. They contained 1 mg of Compound 1 (1.36 mmol) and 1 mg DOPE (1.34 mmol) in 1 ml of 10 mM HEPES, pH 7.8, and complexed with 4 µg of pBS.RSVLux as described above. Transfection was performed in 35 mm dishes. The protein amount shown is the amount of protein in the 20 µl sample that was assayed for luciferase as well. Protein values are also useful indicators of cytotoxicity. The results are shown in Table 3, below. Table 3 shows luciferase activity after transfection into 3T3 cells with Liposome/DNA complexes containing the indicated volumes of liposomes (1:1 molar ratio of Compound 1/DOPE) and 4 µg of pBS.RSVLux. Results with Lipofectin (used at its optimal amount) are shown for comparison.

TABLE 3

| | LUX activity (L.U. × $10^3$) | Protein Amount (µl) | Specific Activity (L.U. × $10^3$/µg protein) |
|---|---|---|---|
| Volume (µl) of Compound 1/Dioleoyl-phosphatidyl-choline | | | |
| 3 | 637 ± 106 | 35.1 ± 4.8 | 18 |
| 5 | 1700 ± 154 | 39.4 ± 3.4 | 43 |
| 10 | 4303 ± 336 | 34.5 ± 4.5 | 125 |
| 20 | 4834 ± 309 | 30.4 ± 1.5 | 159 |
| 30 | 5723 ± 1018 | 33.7 ± 2.3 | 170 |
| Volume (µl) of Lipofectin (DOTMA/Dioleoyl phosphatidyl-choline) | | | |
| 40 | 224 ± 22 | 35.5 ± 1.7 | 6 |

The data in Table 3 show that Compound 1/Dioleoylphosphatidylcholine (1:1) can mediate the transfection of 3T3 cells much more efficiently than Lipofectin.

Luciferase activity was also measured after transfection into 3T3 cells with Liposome/DNA complexes containing the indicated volumes of liposomes (1:2 molar ratio of Compound 1/Dioleoylphosphatidylcholine) and 4 µg of pBS.RSVLux. Results with Lipofectin (used at its optimal amount) are shown for comparison in Table 4, below. Compound 1/Dioleoylphosphatidylcholine liposomes were prepared from 1 mg (1.36 µmol) of Compound 1 and 2 mg (2.69 mmol) of DOPE as above. The experimental conditions of transfection were similar to those above in Table 3.

TABLE 4

| | LUX activity (L.U. × $10^3$) | Protein Amount (µl) | Specific Activity (L.U. × $10^3$/µg protein) |
|---|---|---|---|
| Volume (µl) of Compound 1/Dioleoyl-phosphatidyl-choline (1:2) | | | |
| 5 | 1371 ± 267 | 44.2 ± 1.3 | 31 |
| 10 | 3498 ± 439 | 38.9 ± 0.2 | 90 |

TABLE 4-continued

| | LUX activity (L.U. × $10^3$) | Protein Amount (µl) | Specific Activity (L.U. × $10^3$/µg protein) |
|---|---|---|---|
| 20 | 7624 ± 983 | 39.6 ± 1.4 | 193 |
| 40 | 4728 ± 694 | 20.0 ± 3.9 | 236 |
| 80 | 209 ± 19 | 5.3 ± 2.1 | 39 |
| Volume (µc) of Lipofectin (DOTMA/Dioleoyl-phosphatidyl-choline) | | | |
| 40 | 224 ± 22 | 35.5 ± 1.7 | 6 |

The data Table 4 show that Compound 1/Dioleoylphosphatidylcholine (1:2) can mediate transfection of 3T3 cells much more efficiently than Lipofectin.

Liposomes Compound 1/Dioleoylphosphatidylcholine (1:1) (1.36 umol of Compound 1 and 1.34 umol Dioleoylphosphatidylcholine) and (1:2) (1.36 mmol of Compound 1 and 2.69 mmol of DOPE) were prepared as above. Transfections were performed in 12-well plates and assayed for luciferase as described. The results of these studies are shown in Table 5, below.

TABLE 5

| | LUCIFERASE ACTIVITY (L.U. × $10^3$) | | | | | |
|---|---|---|---|---|---|---|
| Volume of Liposome Formulation (µl) | DOTMA/ Dioleoyl-phospha-tidyl-choline Lipofectin 1 µg DNA | Compound 1/PE (1:1), 1 µg DNA | Compound 1/PE (1:1), 2 µg DNA | Compound 1/PE (1:1) 3 µg DNA | Compound 1/PE (1:2) 1 µg DNA | Compound 1/PE (1:2) 2 µg DNA |
| 4 | | 2704 | 4573 | 5610 | 1358 | 5125 |
| 5 | 496 | | | | | |
| 8 | | 4380 | 9414 | 5678 | 5521 | 5288 |
| 10 | 422 | | | | | |
| 12 | | 2421 | 9175 | 5520 | 4938 | 4774 |
| 16 | | 2045 | 8871 | 5645 | 5653 | 5195 |
| 20 | | 1934 | 5366 | 4394 | 5760 | 3534 |
| 24 | | 1639 | 1457 | 3471 | 6370 | 3883 |

This data in Table 5 show that Compound 1/Dioleoylphosphatidylcholine (same as PE) can mediate the efficient transfection at a wide variety of concentrations of plasmid DNA, amounts of liposome and ratio's of Compound 1/Dioleoylphosphatidylcholine.

β-galactosidase gene expression was determined in 3T3 cells after transfection with various concentrations of pBS.RSVLacZ and Compound 1/Dioleoylphosphatidylcholine liposomes. The transfections were performed as described above using 24-well plates. The activities of β-galactosidase in transfected cells (optical units at 405 nm after 4 hours of incubation at 37° C.) are shown as the mean±range of duplicates in Table 6, below. Amounts of pBS.RSVLacZ plasmid DNA are shown as nmol of nucleotides. Amounts of Compound 1/Dioleoylphosphatidylcholine liposomes are shown as nmol of Compound 1. All liposomes contained a 1:1 molar ratio of Compound 1 to DOPE.

TABLE 6

| Amount of pBS.RSVLacZ | β-Galactosidase Activity With Various Amounts of Compound 1/Dioleoylphosphatidylcholine Formulation (nmol of Compound 1) | | | | |
|---|---|---|---|---|---|
| (nmol) | 117 | 55 | 29 | 15 | 7 |
| 34 | 1.11 ± 0.09 | 2.24 ± 0.07 | 1.32 ± 0.35 | 1.31 ± 0.35 | 0.67 ± 0.23 |
| 17 | 0.14 ± 0.05 | 0.77 ± 0.31 | 1.62 ± 0.04 | 1.90 ± 0.15 | 1.08 ± 0.06 |
| 8.6 | 0.04 ± 0.01 | — | 1.12 ± 0.32 | 1.60 ± 0.07 | 1.11 ± 0.04 |
| 4.3 | 0.20 ± 0.04 | 0.36 ± 0.16 | 1.06 ± 0.16 | 1.49 ± 0.35 | 1.50 ± 0.01 |
| 2.1 | 0.06 ± 0.02 | 0.26 ± 0.05 | 0.77 ± 0.12 | 1.29 ± 0.16 | 0.96 ± 0.15 |

The data in Table 6 show that Compound 1/Dioleoylphosphatidylcholine (same as PE in all cases) can mediate the efficient transfection at a wide variety of concentrations of plasmid DNA, amounts of liposome and ratio's of Compound 1/Dioleoylphosphatidylcholine. The results using another reporter gene system confirms the results using the luciferase reporter system.

EXAMPLE 6

Compound 1/Dioleoylphosphatidylcholine liposomes can mediate the transfection of DNA into a wide variety of cells in culture Liposomes were prepared and various cell lines were transfected using the procedures set forth above in Examples 3, 4 and 5. A comparison of transfection efficiency of various mammalian cell lines was made with Compound 1/Dioleoylphosphatidylcholine (1:1) and DOTMA/Dioleoylphosphatidylcholine (Lipofectin) liposomes. Results, as shown in Table 7, are expressed as ratio of luciferase activity after Compound 1/Dioleoylphosphatidylcholine-mediated transfection to activity after lipofectin-mediated transfection in the same experiment. The transfections were done as in Table 3.

TABLE 7

| Cell Line | Ratio of Luciferase Activity With Compound 1/Dioleoyl-phosphatidylcholine to DOTMA/Dioleoyl phosphatidyl-choline (Lipofectin) | Standard Deviation | Number of Experiments |
|---|---|---|---|
| 3T3 | 20.90 | ±6.65 | n = 12 |
| COS-7 | 3.05 | ±0.91 | n = 6 |
| HeLa | 15.58 | ±3.61 | n = 2 |
| 293 | 1.47 | ±0.2 | n = 2 |
| HepG2 | 3.81 | ±0.04 | n = 4 |
| Primary Rat Myoblasts | 4.15 | ±0.13 | n = 5 |

The data in Table 7 show that the Compound 1/Dioleoylphosphatidylcholine (1:1) liposome formulation mediates the efficient transfection into a wide variety of cells. In fact, transfection with Compound 1/Dioleoylphosphatidylcholine is more efficient than DOTMA/Dioleoylphosphatidylcholine (Lipofectin) in a wide variety of cells.

EXAMPLE 7

Liposome formulations containing Compound 1 and a variety of neutral phospholipids can mediate efficient DNA transfection The effect of the neutral phospholipid within Compound 1 liposomes on the transfection of pBS.RSVLux into 3T3 cells was studied. Liposomes were prepared as described above with the standard concentration of Compound 1 1.34 mM and various amounts of neutral lipid as indicated. The transfections and luciferase assays on 20 µl of cell extract were performed as described above. The mean luciferase activity from two plates and its range are shown in Table 8, below.

TABLE 8

| Type of Vesicles (mM indicates amount of neutral phospholipid and ratio of lipids shown also) | Luciferase activity (×10³) |
|---|---|
| Compound 1 Vesicles | |
| Compound 1 alone | 2653 ± 156 |
| Compound 1/Dioleoylphosphatidylcholine (1.36 mM) (1:1) | 9294 ± 119 |
| Compound 1/Dioleoylphosphatidylcholine (2.72 mM) (1:2) | 5644 ± 64 |
| Compound 1/Phosphatidylcholine (1.26 mM) (1:1) | 4734 ± 345 |
| DOTMA/DOPE (1:1) | 327 ± 73 |
| DOTMA/Phosphatidylcholine (0.75 mM) (1:1) | 33 ± 22 |

The data in Table 8 show that Compound 1 can mediate the efficient DNA transfection of 3T3 cells either alone or with phosphatidylcholine. Luciferase expression after transfection with Compound 1/phosphatidylcholine was only reduced 50% as compared to expression after transfection with Compound 1/PE. This indicates that Compound 1 is not totally dependent on a fusogenic lipid such as Dioleoylphosphatidylcholine and even works by itself. In comparison, DOTMA could not mediate efficient transfection when used with phosphatidylcholine instead of Dioleoylphosphatidylcholine. That is, luciferase expression after transfection with DOTMA/phosphatidylcholine was reduced ten-fold as compared to expression after transfection with DOTMA/Dioleoylphosphatidylcholine. This suggests that DOTMA requires the use of a fusogenic lipid such as Dioleoylphosphatidylcholine, whereas Compound 1 is not as dependent on the inclusion of a fusogenic lipid.

EXAMPLE 8

Influence of Dioleoylphosphatidylcholine on Compound 20 mediated expression of luciferase in 3T3 cells Liposomes were prepared with standard concentration of Compound 20 1.34 mM as described above. The transfection was performed as described above. Luciferase activity in transfected cells is shown as light units ×10⁻³ per 20 µl of cell lysate.

TABLE 9

| Volume (μl/well) | Compound 20 | Compound 20/Dioleoylphosphatidylcholine (1:0.5) | Compound 20/Dioleoylphosphatidylcholine (1:1) |
|---|---|---|---|
| 2 | 1.5 | 9.9 | 22.8 |
| 4 | 63.9 | 158.1 | 316.2 |
| 7 | 780.0 | 202.7 | 358.7 |
| 10 | 2128.7 | 301.7 | 163.3 |
| 15 | 2092.4 | 400.0 | 108.2 |

These results indicate that Dioleoylphosphatidylcholine actually inhibits the transfection efficiency of Compound 20, which is marked contrast to the pH-insensitive cationic lipids. This implies that the pH-sensitive lipids operate by a different mechanism that the pH-insensitive lipids.

EXAMPLE 9

Several different pH-sensitive cationic lipids within liposomes-mediate the efficient transfection of 3T3 cells A comparison was made of transfection efficiency of 3T3 cells with different pH-sensitive cationic liposomes and DOTMA/Dioleoylphosphatidylcholine (Lipofectin). Results, shown below in Table 10, are expressed as ratio of luciferase activity after transfection with the pH-sensitive cationic liposome relative to activity after transfection with Lipofectin (typically $10^8$ light units per mg of cell protein) in the same experiment. The concentration of the cationic lipids in all compositions was 1.34 mM. The transfection was performed under the conditions described above.

TABLE 10

| Liposome Composition | pBS.RSVLux DNA per well (μg) | Liposomes per well (μl) | Relative efficiency (Lipofectin = 1.0) |
|---|---|---|---|
| Compound 3 | 2 | 10 | 1.71 |
| Compound 3/phosphatidylcholine (1:1) | 2 | 20 | 0.58 |
| Compound 6/Dioleoylphosphatidylcholine (1:1) | 1 | 4 | 0.23 |
| Compound 8/Dioleoylphosphatidylcholine (1:1) | 2 | 40 | 7.68 |
| Compound 8/Dioleoylphosphatidylcholine (1:2) | 2 | 20 | 1.88 |
| Compound 5/Dioleoylphosphatidylcholine (1:1) | 1 | 30 | 0.25 |
| Compound 5/Dioleoylphosphatidylcholine (1:2) | 1 | 30 | 0.84 |
| Compound 5/Dioleoylphosphatidylcholine (1:3) | 1 | 30 | 0.67 |
| Compound 20 | 1 | 10 | 16.2 |
| Compound 21/Dioleoylphosphatidylcholine (1:1) | 1 | 4 | 0.40 |

The data in Table 10 show that several different pH-sensitive cationic lipids within liposomes can mediate the efficient transfection of plasmid DNA as compared to Lipofectin. This shows that pH-sensitive cationic liposomes containing 4 different hydrophobic groups and 3 different pH-sensitive cationic groups enable the efficient transfection of plasmid DNA.

EXAMPLE 10

The effect of serum on efficiency of transfection

Studies were also performed with 293 cells in 6-well plates (35 mm) in three variations:

1. No Serum

1 μg of pBS.RSVLux plasmid DNA in 200 μl of Opti-MEM was mixed with 20 μl of Lipofectin (BRL) or Compound 1/Dioleoylphosphatidylcholine (1:1 molar ratio) in 200 μl of Opti-MEM and incubated for 15 min at room temperature. The mixture was added to the tissue culture plates in 1 ml of Opti-MEM.

2. Serum Before Complex Formation

1 μg of pBS.RSVLux plasmid DNA in 180 μl of Opti-MEM and 20 μl of fetal calf serum (Hyclone) were mixed with 20 μl of Lipofectin or Compound 1/Dioleoylphosphatidylcholine (1:1 molar ratio) (final serum concentration=10%)

3. Serum After Complex Formation

1 μg of pBS.RSVLux plasmid DNA in 200 μl of Opti-MEM and 20 μl of Lipofectin or Compound 1/Dioleoylphosphatidylcholine (1:1 molar ratio) in 200 μl of Opti-MEM were mixed and incubated 15 min at room temperature and added to cells in 900 μl of Opt-MEM and 140 μl of fetal calf serum (final serum concentration=9.7%).

Table 10A shows the effect of timing of serum addition on transfection efficiency.

TABLE 10A

| | Mean Luciferase Activity (L.U.) (±SD) | |
|---|---|---|
| CONDITION | Lipofectin | Compound 1/Dioleoylphosphatidylcholine |
| No Serum | 6863 (±1292) | 8051 (±881) |
| Serum Before | 2738 (±411) | 7170 (±628) |
| Serum After | 6228 (±2227) | 16000 (±100) |

A similar experiment was conducted to explore the effect of various concentrations of fetal calf serum that was added prior to the formation of pBS.RSVLux plasmid DNA-Compound 1/Dioleoylphosphatidylcholine complexes. This experiment was performed as described above. The data in Table 10B shows that even the inclusion of 80% serum did not substantially inhibit transfection efficiency. Increasing the % serum from 20 to 80% did not further decrease transfection efficiency.

TABLE 10B

| Serum Concentration (%) | Mean Luciferase Activity (L.U.) (±SD) |
|---|---|
| 0 | 16540 (±495) |
| 5 | 13450 (±359) |
| 10 | 12250 (±3040) |
| 20 | 11100 (±1414) |
| 40 | 12650 (±2050) |
| 80 | 11650 (±636) |

EXAMPLE 11

Influence of pH on transfection activity of liposomes

This study was performed to determine the effect on transfection efficiency of the pH in which the liposome/plasmid DNA complexes were formed. One μg of pBS.RSVLux in 100 μl of Opti-MEM (pH 7.4) or 30 mM Tris, pH 8.5, was mixed with 100 μl of the same respective buffer containing 20 μl Lipofectin (DOTMA/Dioleoylphosphatidylcholine, Life Technologies, Inc.) or 20 μl of Compound 1/Dioleoylphosphatidylcholine and incubated 30 min. The mixture was added to cells in 600 μl of Opti-MEM. The study was continued so that the pH rapidly decreases after the DNA/liposome complex is added to the culture media (pH 7.4). The results are shown in Table 11, which shows the effect of pH of the media in which the pBS.RSVLux/liposome complexes are formed in.

TABLE 11

| | Luciferase Activity (L.U.)* | |
| --- | --- | --- |
| pH in which liposome/DNA complexes formed | Lipofectin | Compound 1/Dioleoylphosphatidylcholine |
| 7.4 | 813 ± 64 | 4852 ± 271 |
| 8.5 | 509 ± 27 | 7501 ± 321 |

*Luciferase activity in the transfected cells (light units per 20 μl of 200 μl cell extract) is shown as the mean ± standard deviation (n = 2).

The data in Table 11 show that transfection efficiency is increased when the Compound 1/Dioleoylphosphatidylcholine-plasmid DNA complexes are formed at alkaline pH while those of Lipofectin (DOTMA/Dioleoylphosphatidylcholine) are decreased.

EXAMPLE 12

Comparison of Transfection Efficiency and Cellular Toxicity in 3T3 Cells Among Lipofectin, LipofectAMINE, and Compound 1/Dioleoylphosphatidylcholine Transfection Reagents The transfection efficiency of the Lipofectin, LipofectAMINE, and Compound 1/Dioleoylphosphatidylcholine was compared at a wide range of ratios of transfection reagent to DNA. The amount of pBS.RSVLux was kept fixed at 1 μg per well and the amount of transfection reagent was increased at 2.5 μl increments. The 3T3 cells were in 12-well plates and were incubated with the liposome/DNA complexes for six hours. Luciferase activity was determined after two days. The cells were placed into 100 μl of luciferase lysis buffer that did not contain DTT so the protein assays could be performed. After 20 μl were removed for protein assay, 10 μl of 10 mM DTT was added to each sample and 20 μl were assayed for luciferase activity. The means of the two experiments and their standard deviations are shown in Tables 11A and 11B.

TABLE 11A

| | Mean Luciferase Activity (L.U.) (±SD) (×10³) | | |
| --- | --- | --- | --- |
| Liposome Amount (μl) | Lipofectin | LipofectAMINE | Compound 1/Dioleoylphosphatidylcholine |
| 0 | 0.3 (±37) | 0.3 (±0.02) | 0.4 (±0) |
| 2 | 1.0 (±499) | 203 (±10) | 335 (±5) |
| 4 | 9 (±30) | 1,738 (±233) | 1,486 (±15) |
| 6 | 523 (±365) | 3,409 (±429) | 4,274 (±91) |
| 8 | 734 (±221) | 2,145 (±380) | 5,442 (±18) |
| 10 | 333 (±41) | 1,463 (±341) | 5,067 (±571) |

TABLE 11B

| | Mean Protein (μg/20 μl) | | |
| --- | --- | --- | --- |
| Liposome Amount (μl) | Lipofectin | LipofectAMINE | Compound 1/Dioleoylphosphatidylcholine |
| 0 | 18.5 | 11.6 | 14.9 |
| 2 | 18.25 | 11.35 | 15.75 |
| 4 | 14.25 | 10.3 | 15.9 |
| 6 | 14.25 | 6.05 | 16.6 |
| 8 | 14.1 | 3.5 | 14.15 |
| 10 | 13.3 | 4.05 | 12.95 |

To be sure that optimal amounts of liposome formulations were used, it was necessary to compare a wide range of liposome amounts. Optimal amounts are determined when a maximum inflection point is reached. This was obtained in Table 11A for all three formulations. The results clearly indicate that Compound 1/PE enables higher transfection efficiency than the other two cationic lipid formulations which are considered to be the best commercially-available reagents at this time. The other important factor is the cellular toxicity of the transfection reagents and these results are shown in Table 11B. A simple but very informative measure of cellular toxicity is to determine the protein amounts in the cells after exposure to the reagents. A significant decrease in protein amount indicates either cellular death or decreased protein synthesis.

The results in Table 11B clearly show that LipofectAMINE had considerable cellular toxicity. Examination under phase contrast microscope indicated that the decreased protein amounts correlated with decreased numbers of cells on the plates after two days. This indicates that a 6 hour exposure to LipofectAMINE causes more than a 50% reduction in cellular survival two days after exposure. This substantial cellular toxicity occurred at liposome amounts required for optimal transfection efficiency (i.e. 6 μl ).

Given that LipofectAMINE is one of the most efficient transfection reagents, our formulation consisting of Compound 1/Dioleoylphosphatidylcholine is superior in terms of transfection efficiency and cellular toxicity to previously described transfection reagents.

EXAMPLE 13

Compound 1/Dioleoylphosphatidylcholine liposome—mediated RNA transfection

Luciferase mRNA (uncapped) were transcribed from a linear PstI digested plasmid EMCLucBgAn with Large Scale in vitro Transcription Kits (Ambion). The Compound 1/Dioleoylphosphatidylcholine (1:1) liposomes were prepared as described above. Liposomes and 5 μg of synthetic mRNA were added to 100 μl of Opti-MEM and then mixed with 100 μl of Opti-MEM which contained different amount of the liposomes. The mixture was incubated 15 min. at 20° C. and added to 3T3 cells to 600 μl of Opti-MEm. Transfections were performed with 12 wells plates (25 mm). The monolayers were about to reach confluence. The cells were incubated with the RNA/liposomes mixture for 8 hours. Then cells were harvested and luciferase activity was determined as described above. Luciferase activity in transfected cells (light units for 20 μl cells lysate×10³) is shown as the mean±range of duplicates in Table 12.

TABLE 12

| Volume of liposomes (μl) | Lipofectin | Compound 1/Dioleoylphosphatidylcholine |
|---|---|---|
| 1 | 7 ± 1 | 5 ± 1 |
| 2 | 37 ± 3 | 17 ± 2 |
| 4 | 109 ± 11 | 62 ± 9 |
| 8 | 247 ± 21 | 270 ± 17 |
| 12 | 25 ± 14 | 276 ± 3 |

These results indicate that Compound 1/Dioleoylphosphatidylcholine can transfect RNA efficiently.

EXAMPLE 14

Compound 1/Dioleoylphosphatidylcholine pH-sensitive cationic liposomes are endocytosed and then release their internal contents Sulfonyl rhodamine was incorporated into Compound 1/Dioleoylphosphatidylcholine liposomes by standard methods and then applied to 3T3 cells in culture. At various times after exposure at 37° C., the cells were visualized using a fluorescent microscope. At 30 min after exposure, fluorescence was observed within cells. The pattern of staining showed multiple particles that were consistent with inclusion of the rhodamine within vesicles such as endosomes or lysosomes. This pattern was seen in almost all the cells. By three hours after exposure, many of the cells contained a diffuse pattern of staining consistent with release of the rhodamine from the vesicles.

These results were compared to those using the pH-insensitive cationic liposome lipofectin. Rhodamine labelling was also seen in vesicle but the intensity and number of fluorescent vesicles per cell was substantially less than that with Compound 1/Dioleoylphosphatidylcholine. At 30 min, approximately 1% of the cells also contained diffuse staining. At 3 hours after exposure, there was no increase in the number of cells with diffuse staining, in contrast to the experience with Compound 1/Dioleoylphosphatidylcholine. These results would suggest that lipofectin was able to fuse directly with the cell membrane of a small percentage of cells but that they were not efficiently released from vesicles.

In summary, these results are consistent with the hypothesis that pH-sensitive, cationic liposomes can be released from acidic endosomes efficiently. This mechanism differs from the mechanism of pH-insensitive, cationic liposomes. These studies also demonstrate that a small molecule can be delivered to cells.

EXAMPLE 15

Compound 6/Dioleoylphosphatidylcholine liposomes enhances the transfection of plasmid DNA into mouse muscle in vivo and in situ A screening program was used to discover delivery systems that increase the transfection efficiency of plasmid DNA into muscle cells in vivo. 10 μg of plasmid pBS.RSVLux DNA in 50 μl of normal saline solution was injected into the quadriceps muscle of young adult mice. After 2 minutes, 50 μl of normal saline solution containing 0, 20 (condition B in Table 12A), 60 and 180 μg of lipids (Compound 6 and Dioleoylphosphatidylcholine in equal concentration) were injected in same place. After 7 days, the entire quadricep muscles were excised and an extract was prepared in 200 μl of lysis buffer described above.

Values are the mean of luciferase activity in six injected muscles and ±indicats standard deviation (SD) (n=2). After injection of 10 μg of pBS.RSVLux, normal saline was injected containing 0, 20, 60, and 180 μg of liposome.

TABLE 12A

| Amount of Compound 6/Dioleoylphosphatidylcholine Liposomes (μg) | Mean Luciferase Activity (L.U.) × 10$^3$ (±SD) |
|---|---|
| 0 | 80 (±34) |
| 20 | 279 (±198) |
| 60 | 451 (±215) |
| 180 | 508 (±261) |

The results of Table 12A show that Compound 6/Dioleoylphosphatidylcholine liposomes injected soon after plasmid DNA injection greatly increased the transfection efficiency. This is in marked contrast to the injection of Lipofectin (DOTMA/Dioleoylphosphatidylcholine), which completely inhibited the expression of plasmid previously injected to background levels of L.U. of 500 (n=6). This is consistent with previous results in which the co-injection of Lipofectin and pBS.RSVLux completely inhibited luciferase expression.

The results in Table 12A are also consistent with the results shown in Example 11. The ability for the Compound 1/Dioleoylphosphatidylcholine to form transfection-active DNA complexes in the presence of serum is consistent with the ability of Compound 6/Dioleoylphosphatidylcholine liposomes to form active transfection complexes in situ in muscle tissue. Muscle tissue is rich in negatively-charged extracellular matrix material (such as chondroitin sulfate), which has been shown to greatly inhibit the formation of transfection-competent DOTMA/Dioleoylphosphatidylcholine-DNA complexes.

EXAMPLE 16

Comparison of the pK of various compounds with their ability to mediate the transfection of mammalian cells.

4–5 μmoles of compounds 1, 4, 5, 6 or 8 in a chloroform solution were dried in separate 1.5 ml microcentrifuge tubes under a vacuum overnight. The dried compounds were dissolved in 3 ml of a 0.5% water solution of Triton X-100, pH 3.5. A 20 mM NaOH solution was added to each tube using a Dilutor 401 (Gilson Co.) and the pH was monitored using a Beckman φ 72 pH meter. The pKa's of the compounds were determined from differential titration curves. The transfections of the 3T3 cells were done with liposome preparations containing Dioleoylphosphatidylcholine as described above. The results are shown below in Table 13.

TABLE 13

| Compound | pK of Compound | Relative Transfection Efficiency (Lipofectin = 1.0) | Relative Dioleoylphosphatidylcholine Content in the Liposomes |
|---|---|---|---|
| 1 | 7.1 | 20.9 | 1:1 |
| 4 | <3.5 | 0 | 1:1 |
| 5 | 6.8 | 0.84 | 1:2 |
| 6 | 6.0 | 0.23 | 1:1 |
| 8 | 5.3 | 7.68 | 1:1 |

Examples have been included to illustrate preferred modes of the invention. Certain aspects of the Examples are described in terms of techniques and procedures found or contemplated by the present inventors to work well in the practice of the invention. These examples are exemplified through the use of standard laboratory practices of the inventor. In light of the present disclosure and the general level of skill in the art, those of skill will appreciate that the Examples are intended to be exemplary only and that numerous changes, modifications and alterations can be employed without departing from the spirit and scope of the invention.

What is claimed is:

1. A compound having a pKa from 4.0 to 8.0 and having the formula:

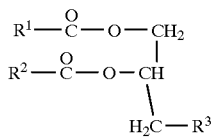

wherein $R^1$ and $R^2$ are independently $CH_3(CH_2)_{14}$, $CH_3(CH_2)_{12}$ or $CH_3(CH_2)_7CHCH(CH_2)_7$; and $R^3$ is 1-methylimidazole, imidazole, 4,9-dioxo-1,12-dodecanediamine, cysteamine, 1-(3-aminopropyl) imidazole, morpholine, 4-aminopyridine, pyridine, guanidine, hydrazine, thiuronium or piperazine.

2. A compound having the structure:

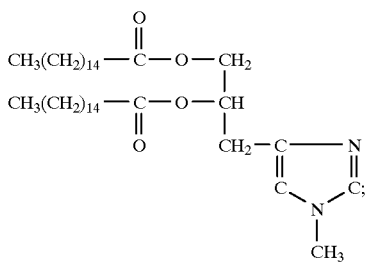

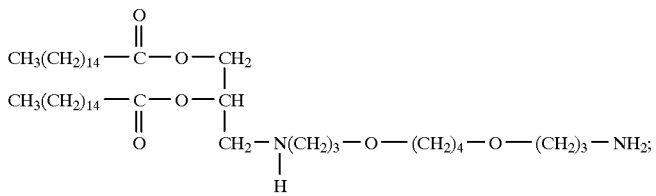

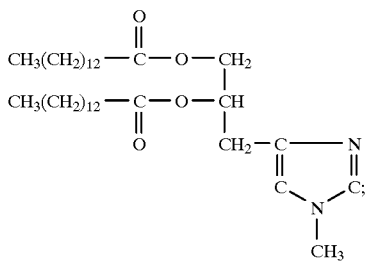

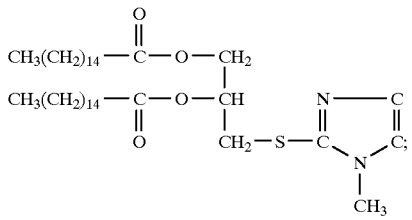

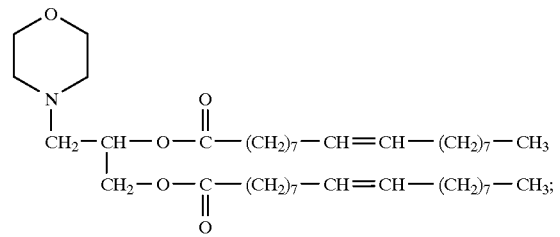

-continued
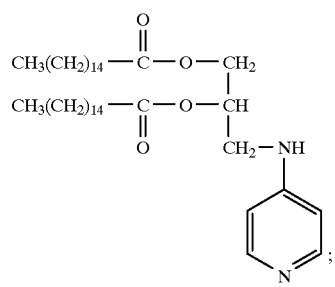
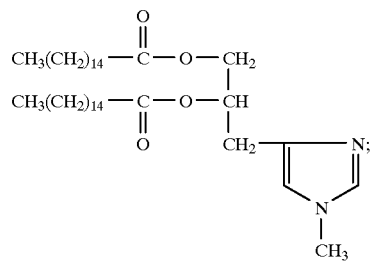
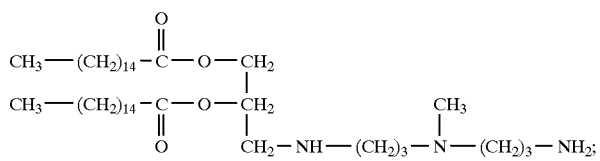
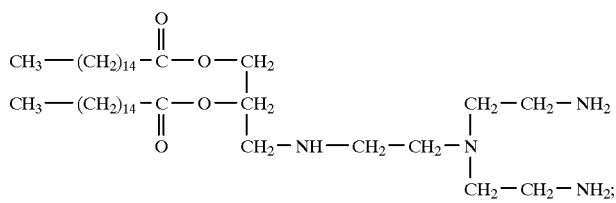
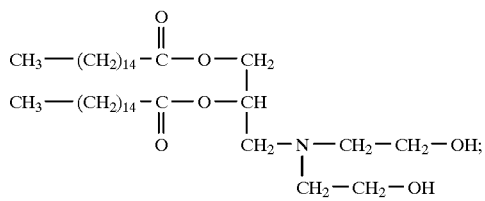
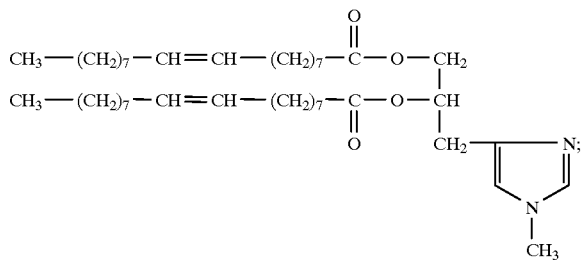
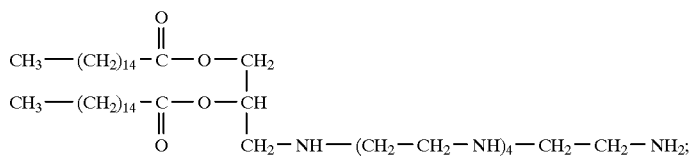

-continued

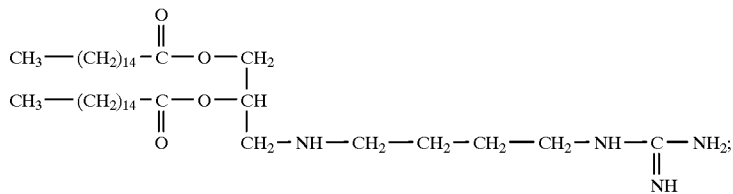

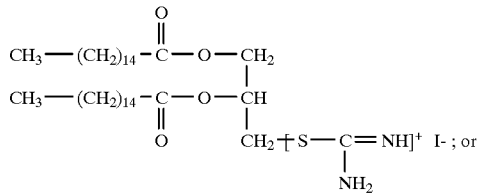

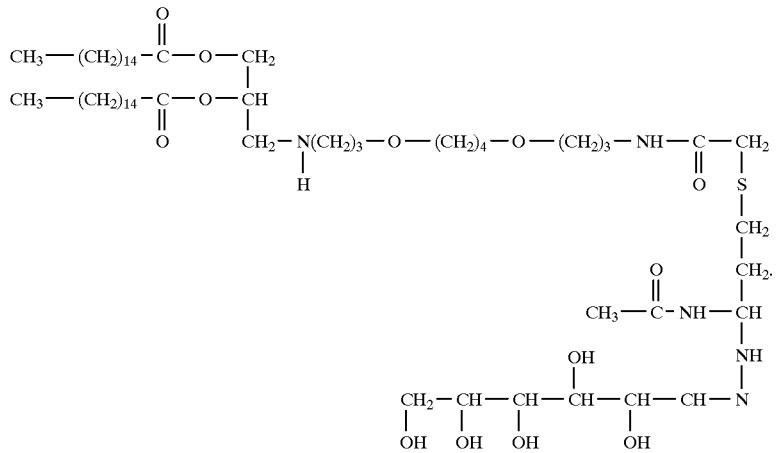

glucose derivative

3. A compound having a pKa from 4.0 to 8.0 and having the formula:

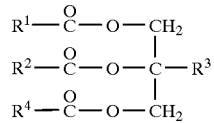

III wherein $R^1$ and $R^2$ and $R^4$ are independently $CH_3(CH_2)_{14}$, $CH_3(CH_2)_{12}$ or $CH_3(CH_2)_7CHCH(CH_2)_7$; and $R^3$ is Tris(2-aminoethyl)amine, 3,3'-diamino-N-methyldipropylamine, hydroxylamine, diethanol amine or pentaethylenehexamine.

4. A compound having the structure:

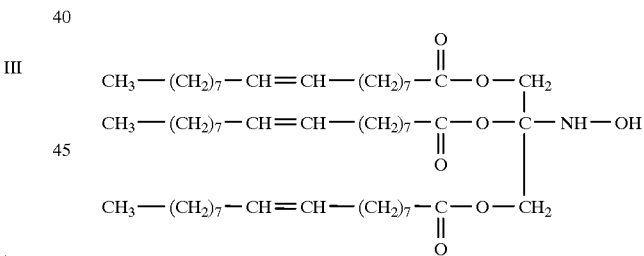

5. A compound having the structure:

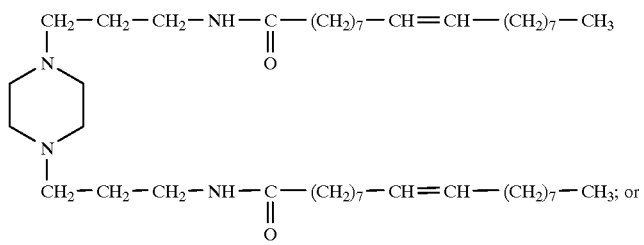

-continued
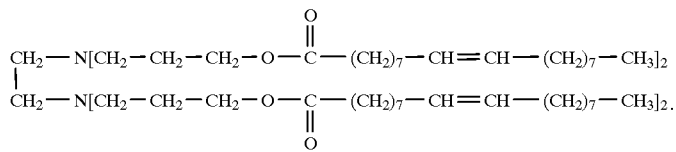
6. A compound having the structure:
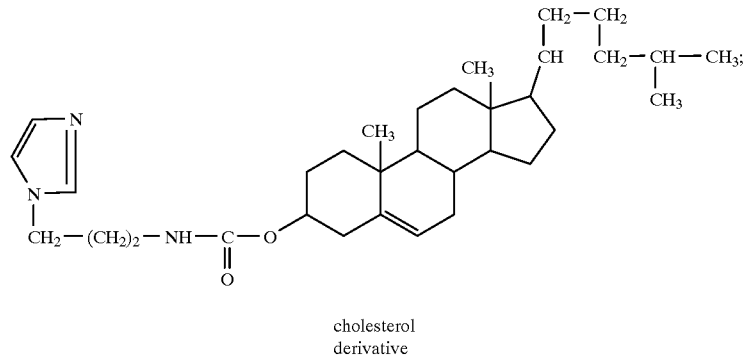
cholesterol derivative
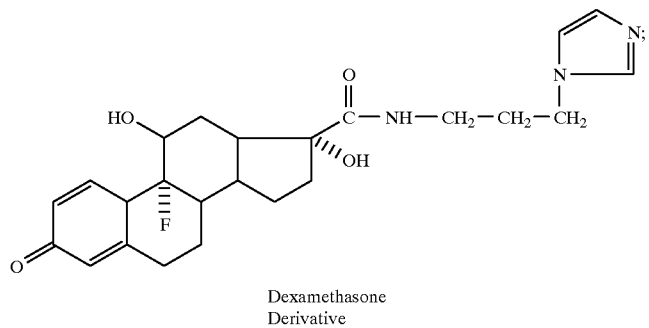
Dexamethasone Derivative
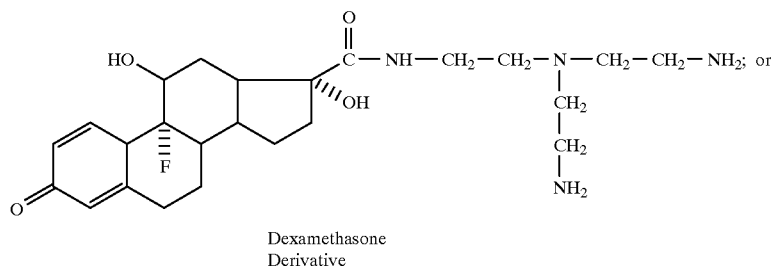
Dexamethasone Derivative -continued
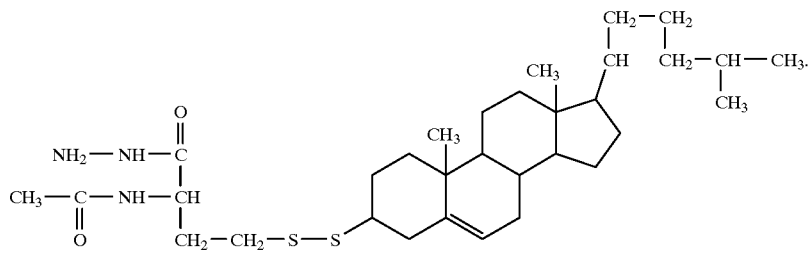
cholesterol derivative
7. An amphipathic compound having the structure:
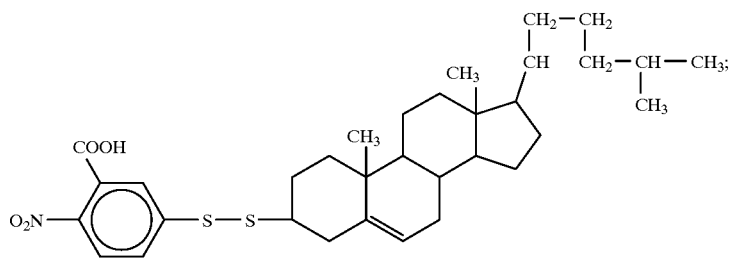
cholesterol derivative
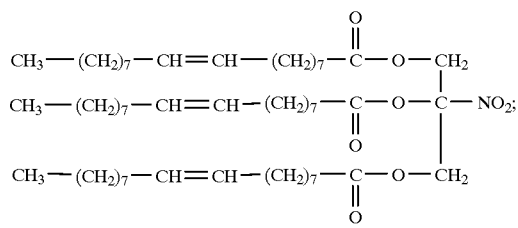
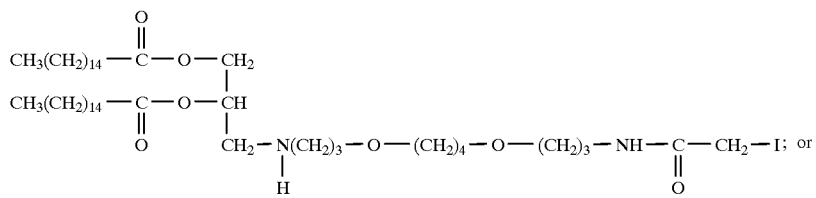

-continued

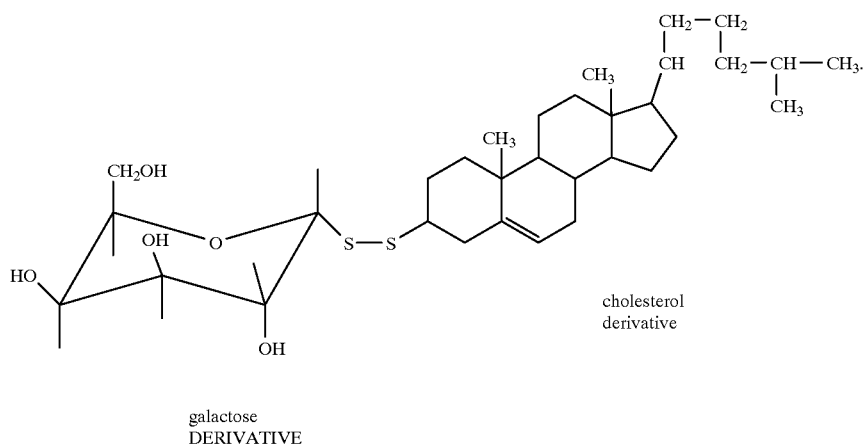

galactose DERIVATIVE

8. A delivery system for biologically active substances comprising a plurality of vesicles, wherein each vesicle contains an amphipathic compound of claim 1.

9. A delivery system for biologically active substances comprising a plurality of vesicles, wherein each vesicle contains an amphipathic compound of claim 3.

10. A delivery system for biologically active substances comprising a plurality of vesicles, wherein each vesicle contains an amphipathic compound of claim 3.

11. A delivery system for biologically active substances comprising a plurality of vesicles, wherein each vesicle contains an amphipathic compound of claim 4.

12. A delivery system for biologically active substances comprising a plurality of vesicles, wherein each vesicle contains an amphipathic compound of claim 5.

13. A delivery system for biologically active substances comprising a plurality of vesicles, wherein each vesicle contains an amphipathic compound of claim 6.

14. A delivery system for biologically active substances comprising a plurality of vesicles, wherein each vesicle contains an amphipathic compound of claim 7.

* * * * *